(12) United States Patent
Davenport et al.

(10) Patent No.: US 8,915,906 B2
(45) Date of Patent: *Dec. 23, 2014

(54) METHOD FOR TREATMENT OF POST-PARTUM ABDOMINAL SKIN REDUNDANCY OR LAXITY

(75) Inventors: Scott A. Davenport, Half Moon Bay, CA (US); David A. Gollnick, San Francisco, CA (US); Michael Levernier, San Francisco, CA (US); Gregory J. R. Spooner, Kensington, CA (US)

(73) Assignee: Cutera, Inc., Brisbane, CA (US)

(*) Notice: Subject to any disclaimer, the term of this patent is extended or adjusted under 35 U.S.C. 154(b) by 382 days.

This patent is subject to a terminal disclaimer.

(21) Appl. No.: 11/199,344

(22) Filed: Aug. 8, 2005

(65) Prior Publication Data

US 2006/0052847 A1  Mar. 9, 2006

Related U.S. Application Data

(63) Continuation-in-part of application No. 10/996,549, filed on Nov. 23, 2004, now Pat. No. 7,722,600, which is a continuation-in-part of application No. 10/789,139, filed on Feb. 27, 2004.

(60) Provisional application No. 60/540,981, filed on Jan. 30, 2004, provisional application No. 60/497,745, filed on Aug. 25, 2003, provisional application No. 60/601,352, filed on Aug. 13, 2004.

(51) Int. Cl.
*A61B 18/18* (2006.01)
*A61B 18/00* (2006.01)
*A61B 18/20* (2006.01)
*A61B 17/00* (2006.01)

(52) U.S. Cl.
CPC ....... *A61B 18/203* (2013.01); *A61B 2018/0047* (2013.01); *A61B 2018/1807* (2013.01); *A61B 2018/208* (2013.01); *A61B 2018/00023* (2013.01); *A61B 2017/00199* (2013.01); *A61B 2018/00452* (2013.01)

USPC ................................ 606/9; 606/11; 128/898

(58) Field of Classification Search
USPC ........................... 128/898; 606/9; 607/88–94
See application file for complete search history.

(56) References Cited

U.S. PATENT DOCUMENTS

| 1,800,277 A | 4/1931 | Boerstler |
| 2,699,771 A | 1/1955 | Rüttger-Pelli ............... 128/24.1 |

(Continued)

FOREIGN PATENT DOCUMENTS

| CA | 968854 | 6/1975 | ........................ 326/4 |
| CA | 1041610 | 10/1978 | ..................... 326/16 |

(Continued)

OTHER PUBLICATIONS

Laser skin resurfacing; Seminars in Cutaneous Medicine and Surgery, vol. 15, Issue 3, Sep. 1996, pp. 177-188 Jeffrey S. Dover and George J. Hruza.*

(Continued)

*Primary Examiner* — David Shay
(74) *Attorney, Agent, or Firm* — Morrison & Foerster LLP

(57) ABSTRACT

A system and method for providing treatments of electromagnetic radiation to areas of post-partum abdominal skin. The treatments provide for raising the temperature in a portion of post-partum abdominal skin to a treatment temperature, which is sufficient to reduce the laxity or redundancy of the post-partum skin. In one embodiment the treatment can provide treatment exposures to sub-areas, of an area of post-partum abdominal skin which has been identified for treatment, and bring a temperature of the tissue being treated to at 50° C.

21 Claims, 16 Drawing Sheets

(56) References Cited

U.S. PATENT DOCUMENTS

| | | | |
|---|---|---|---|
| 3,327,712 A | 6/1967 | Kaufman et al. | 128/398 |
| 3,538,919 A | 11/1970 | Meyer | 606/36 |
| 3,648,706 A | 3/1972 | Holzer | 128/395 |
| 3,693,623 A | 9/1972 | Harte et al. | 128/303.1 |
| 3,834,391 A | 9/1974 | Block | 606/9 |
| 3,867,948 A | 2/1975 | Kallenborn | 128/395 |
| 3,900,034 A | 8/1975 | Katz et al. | 607/89 |
| 4,020,383 A | 4/1977 | Labadini et al. | 313/344 |
| 4,022,534 A | 5/1977 | Kishner | 356/210 |
| 4,122,853 A | 10/1978 | Smith | 606/4 |
| 4,233,493 A | 11/1980 | Nath | 219/354 |
| 4,298,005 A | 11/1981 | Mutzhas | 128/396 |
| 4,388,924 A | 6/1983 | Weissman et al. | 606/9 |
| 4,461,294 A | 7/1984 | Baron | 606/5 |
| 4,505,545 A | 3/1985 | Salia-Munoz | 350/321 |
| 4,539,987 A | 9/1985 | Nath et al. | 128/303.1 |
| 4,608,978 A | 9/1986 | Rohr | 128/303.1 |
| 4,608,990 A | 9/1986 | Elings | 128/633 |
| 4,617,926 A | 10/1986 | Sutton | 606/9 |
| 4,658,823 A | 4/1987 | Beddoe et al. | 128/396 |
| 4,667,658 A | 5/1987 | Guibert | 128/24.1 |
| 4,686,986 A | 8/1987 | Fenyö et al. | 128/396 |
| 4,717,863 A | 1/1988 | Zeiler | |
| 4,733,660 A | 3/1988 | Itzkan | 606/9 |
| 4,747,660 A | 5/1988 | Nishioka et al. | 350/96.25 |
| 4,757,431 A | 7/1988 | Cross et al. | 362/261 |
| 4,784,135 A | 11/1988 | Blum et al. | 128/303.1 |
| 4,813,412 A | 3/1989 | Yamazaki et al. | 128/303.13 |
| 4,819,669 A | 4/1989 | Politzer | 132/200 |
| 4,829,262 A | 5/1989 | Furumoto | 330/4.3 |
| 4,860,172 A | 8/1989 | Schlager et al. | 362/32 |
| 4,884,568 A | 12/1989 | Hahn | 128/303.1 |
| 4,917,084 A | 4/1990 | Sinofsky | 606/7 |
| 4,930,504 A | 6/1990 | Diamantopoulos et al. | 128/395 |
| 4,950,880 A | 8/1990 | Hayner | 250/201.9 |
| 4,976,709 A | 12/1990 | Sand | 606/5 |
| 5,000,752 A | 3/1991 | Hoskin et al. | 606/9 |
| 5,057,104 A | 10/1991 | Chess | 606/9 |
| 5,059,192 A | 10/1991 | Zaias | 606/9 |
| 5,139,494 A | 8/1992 | Freiberg | 606/3 |
| 5,161,526 A | 11/1992 | Hellwing et al. | 128/395 |
| 5,182,857 A | 2/1993 | Simon | 30/34.05 |
| 5,207,671 A | 5/1993 | Franken et al. | 606/9 |
| 5,217,455 A | 6/1993 | Tan | 606/9 |
| 5,226,907 A | 7/1993 | Tankovich | 606/133 |
| 5,258,989 A | 11/1993 | Raven | 372/6 |
| 5,259,380 A | 11/1993 | Mendes et al. | 607/115 |
| 5,282,797 A | 2/1994 | Chess | 606/9 |
| 5,290,273 A | 3/1994 | Tan | 606/9 |
| 5,304,169 A | 4/1994 | Sand | 606/5 |
| 5,304,170 A | 4/1994 | Green | 606/9 |
| 5,312,395 A | 5/1994 | Tan et al. | 606/9 |
| 5,320,618 A | 6/1994 | Gustafsson | 606/9 |
| 5,336,217 A | 8/1994 | Buys et al. | 606/9 |
| 5,337,741 A | 8/1994 | Diamond | 600/8 |
| 5,344,418 A | 9/1994 | Ghaffari | 606/9 |
| 5,344,434 A | 9/1994 | Talmore | 607/88 |
| 5,374,265 A | 12/1994 | Sand | 606/5 |
| 5,397,327 A | 3/1995 | Koop et al. | 606/17 |
| 5,405,368 A | 4/1995 | Eckhouse | 607/88 |
| 5,409,479 A | 4/1995 | Dew et al. | 606/9 |
| 5,425,728 A | 6/1995 | Tankovich | 606/9 |
| 5,441,531 A | 8/1995 | Zarate et al. | 607/90 |
| 5,458,596 A | 10/1995 | Lax et al. | 606/31 |
| 5,474,549 A | 12/1995 | Ortiz et al. | 606/9 |
| 5,486,172 A | 1/1996 | Chess | 606/20 |
| 5,511,563 A | 4/1996 | Diamond | 128/848 |
| 5,522,813 A | 6/1996 | Trelles | 606/2 |
| 5,527,350 A | 6/1996 | Grove et al. | 607/89 |
| 5,569,979 A | 10/1996 | Scott et al. | 313/636 |
| 5,572,091 A | 11/1996 | Langer et al. | 313/636 |
| 5,591,157 A | 1/1997 | Hennings et al. | 606/3 |
| 5,595,568 A | 1/1997 | Anderson et al. | 606/9 |
| 5,611,795 A | 3/1997 | Slatkine et al. | 606/9 |
| 5,620,478 A | 4/1997 | Eckhouse | 607/88 |
| 5,660,836 A | 8/1997 | Knowlton | 424/400 |
| 5,683,380 A | 11/1997 | Eckhouse et al. | 606/9 |
| 5,735,844 A | 4/1998 | Anderson et al. | 606/9 |
| 5,755,753 A | 5/1998 | Knowlton | 607/98 |
| 5,769,844 A | 6/1998 | Ghaffari | 606/16 |
| 5,769,878 A | 6/1998 | Kamei | 607/88 |
| 5,782,895 A | 7/1998 | Zarate et al. | 607/88 |
| 5,807,261 A | 9/1998 | Benaron et al. | 600/473 |
| 5,807,393 A | 9/1998 | Williamson, IV et al. | |
| 5,810,801 A | 9/1998 | Anderson et al. | 606/9 |
| 5,814,040 A | 9/1998 | Nelson et al. | 606/9 |
| 5,820,625 A | 10/1998 | Izawa et al. | 606/9 |
| 5,830,208 A | 11/1998 | Muller | 606/9 |
| 5,843,074 A | 12/1998 | Cocilovo | 606/10 |
| 5,843,143 A | 12/1998 | Whitehurst | 607/88 |
| 5,849,029 A | 12/1998 | Eckhouse et al. | |
| 5,860,967 A | 1/1999 | Zavislan et al. | 606/9 |
| 5,885,274 A | 3/1999 | Fullmer et al. | 606/9 |
| 5,919,219 A | 7/1999 | Knowlton | 607/102 |
| 5,964,749 A | 10/1999 | Eckhouse et al. | 606/9 |
| 5,989,283 A | 11/1999 | Wilkens | 607/88 |
| 6,015,404 A | 1/2000 | Altshuler et al. | 606/9 |
| 6,050,990 A | 4/2000 | Tankovich et al. | 606/9 |
| 6,080,146 A | 6/2000 | Altshuler et al. | 606/9 |
| 6,080,147 A | 6/2000 | Tobinick | 606/9 |
| 6,096,029 A | 8/2000 | O'Donnell, Jr. | |
| 6,096,066 A | 8/2000 | Chen et al. | 607/88 |
| 6,120,497 A | 9/2000 | Anderson et al. | 606/9 |
| 6,168,590 B1 | 1/2001 | Neev | 606/9 |
| 6,171,332 B1 | 1/2001 | Whitehurst | 607/89 |
| 6,228,074 B1 | 5/2001 | Almeida | 606/9 |
| 6,235,015 B1 | 5/2001 | Mead, III et al. | 606/9 |
| 6,241,753 B1 | 6/2001 | Knowlton | 607/99 |
| 6,273,884 B1 | 8/2001 | Altshuler et al. | 606/9 |
| 6,280,438 B1 | 8/2001 | Eckhouse et al. | 606/9 |
| 6,309,387 B1 | 10/2001 | Eggers et al. | |
| 6,311,090 B1 | 10/2001 | Knowlton | |
| 6,319,273 B1 | 11/2001 | Chen et al. | 607/88 |
| 6,334,074 B1 * | 12/2001 | Spertell | 607/101 |
| 6,338,731 B1 | 1/2002 | Laufer et al. | |
| 6,375,672 B1 * | 4/2002 | Aksan et al. | 607/96 |
| 6,377,855 B1 | 4/2002 | Knowlton | 607/101 |
| 6,381,498 B1 | 4/2002 | Knowlton | 607/101 |
| 6,383,176 B1 | 5/2002 | Connors et al. | 606/9 |
| 6,387,089 B1 | 5/2002 | Kreindel et al. | 606/9 |
| 6,402,739 B1 | 6/2002 | Neev | |
| 6,405,090 B1 | 6/2002 | Knowlton | 607/102 |
| 6,413,253 B1 | 7/2002 | Koop et al. | 606/27 |
| 6,413,268 B1 | 7/2002 | Hartman | |
| 6,436,094 B1 | 8/2002 | Reuter | |
| 6,443,978 B1 | 9/2002 | Zharov | 607/91 |
| 6,453,202 B1 | 9/2002 | Knowlton | 607/102 |
| 6,461,866 B1 | 10/2002 | Whitehurst | 435/325 |
| 6,482,199 B1 | 11/2002 | Neev | 606/10 |
| 6,485,484 B1 | 11/2002 | Connors et al. | 606/9 |
| 6,508,813 B1 | 1/2003 | Altshuler | 606/9 |
| 6,511,475 B1 | 1/2003 | Altshuler et al. | 606/9 |
| 6,517,532 B1 | 2/2003 | Altshuler et al. | 606/9 |
| 6,524,329 B1 | 2/2003 | Benedict | 607/88 |
| 6,558,372 B1 | 5/2003 | Altshuler | 606/2 |
| 6,569,155 B1 | 5/2003 | Connors et al. | 606/9 |
| 6,602,275 B1 | 8/2003 | Sullivan | 607/88 |
| 6,605,080 B1 | 8/2003 | Altshuler et al. | 606/3 |
| 6,648,904 B2 | 11/2003 | Altshuler et al. | 607/96 |
| 6,653,618 B2 | 11/2003 | Zenzie | 250/221 |
| 6,659,999 B1 | 12/2003 | Anderson et al. | |
| 6,663,620 B2 | 12/2003 | Altshuler et al. | 606/9 |
| 6,723,090 B2 | 4/2004 | Altshuler et al. | 606/9 |
| 6,743,222 B2 | 6/2004 | Durkin et al. | 606/9 |
| 6,745,078 B1 | 6/2004 | Buchner | |
| 6,749,624 B2 | 6/2004 | Knowlton | 607/104 |
| 6,920,883 B2 * | 7/2005 | Bessette et al. | 128/898 |
| 6,997,923 B2 * | 2/2006 | Anderson et al. | 606/9 |
| 7,147,654 B2 | 12/2006 | Baumgardner et al. | |
| 7,217,266 B2 | 5/2007 | Anderson et al. | |
| 2001/0014819 A1 * | 8/2001 | Ingle et al. | 607/99 |
| 2002/0002367 A1 * | 1/2002 | Tankovich et al. | 606/3 |
| 2002/0019625 A1 | 2/2002 | Azar | |
| 2002/0055092 A1 | 5/2002 | Hochman | 435/4 |

(56) References Cited

U.S. PATENT DOCUMENTS

| | | | |
|---|---|---|---|
| 2002/0091377 A1 | 7/2002 | Anderson et al. | 606/9 |
| 2002/0128635 A1 | 9/2002 | Altshuler et al. | 606/9 |
| 2002/0161357 A1 | 10/2002 | Anderson et al. | 606/9 |
| 2002/0173780 A1 | 11/2002 | Altshuler et al. | 606/9 |
| 2002/0198575 A1 | 12/2002 | Sullivan | 607/88 |
| 2003/0004499 A1 | 1/2003 | McDaniel | 606/3 |
| 2003/0023283 A1 | 1/2003 | McDaniel | 607/88 |
| 2003/0028228 A1* | 2/2003 | Sand | 607/89 |
| 2003/0032900 A1 | 2/2003 | Ella | 601/6 |
| 2003/0032950 A1 | 2/2003 | Altshuler et al. | 606/9 |
| 2003/0045916 A1 | 3/2003 | Anderson et al. | 607/89 |
| 2003/0055413 A1 | 3/2003 | Altshuler et al. | 606/9 |
| 2003/0055414 A1 | 3/2003 | Altshuler et al. | 606/9 |
| 2003/0057875 A1 | 3/2003 | Inochkin et al. | 315/224 |
| 2003/0065313 A1 | 4/2003 | Koop et al. | 606/9 |
| 2003/0065314 A1 | 4/2003 | Altshuler et al. | 606/9 |
| 2003/0069618 A1* | 4/2003 | Smith et al. | 607/100 |
| 2003/0125788 A1 | 7/2003 | Long | 607/133 |
| 2003/0130709 A1 | 7/2003 | D.C. et al. | 607/88 |
| 2003/0195494 A1 | 10/2003 | Altshuler et al. | 606/9 |
| 2003/0199859 A1 | 10/2003 | Altshuler et al. | 606/9 |
| 2004/0010298 A1 | 1/2004 | Altshuler et al. | 607/88 |
| 2004/0024388 A1 | 2/2004 | Altshuler | 606/2 |
| 2004/0034319 A1 | 2/2004 | Anderson et al. | 604/20 |
| 2004/0093042 A1* | 5/2004 | Altshuler et al. | 607/88 |
| 2004/0143247 A1 | 7/2004 | Anderson et al. | |
| 2004/0147985 A1 | 7/2004 | MacFarland et al. | 607/90 |
| 2004/0199152 A1* | 10/2004 | Key | 606/9 |
| 2005/0049658 A1 | 3/2005 | Connors et al. | |
| 2005/0107850 A1 | 5/2005 | Vaynberg et al. | |
| 2005/0107852 A1* | 5/2005 | Levernier et al. | 607/89 |
| 2005/0143793 A1* | 6/2005 | Korman et al. | 607/94 |
| 2005/0154382 A1* | 7/2005 | Altshuler et al. | 606/9 |
| 2005/0171581 A1 | 8/2005 | Connors et al. | 607/88 |
| 2005/0245997 A1* | 11/2005 | Holjo et al. | 607/88 |
| 2006/0052847 A1 | 3/2006 | Davenport et al. | |

FOREIGN PATENT DOCUMENTS

| | | | | |
|---|---|---|---|---|
| DE | 33 47 730 A1 | 7/1985 | | A61N 5/06 |
| DE | 38 03 763 A1 | 8/1989 | | A61N 5/06 |
| DE | 39 06 860 A1 | 9/1989 | | A61B 6/00 |
| EP | 0 565 331 A2 | 4/1993 | | A61N 5/06 |
| GB | 2 360 946 A | 10/2001 | | A61N 5/01 |
| JP | 4-98795 | 3/1992 | | H05B 41/24 |
| JP | 4-322668 | 11/1992 | | A61N 5/06 |
| WO | WO 86/02783 | 5/1986 | | H01S 3/08 |
| WO | WO 89/00871 | 2/1989 | | A61N 5/06 |
| WO | WO 95/15725 | 6/1995 | | A61B 17/41 |
| WO | WO 96/22813 | 8/1996 | | A61N 5/06 |
| WO | WO 97/37723 | 10/1997 | | A61N 5/06 |
| WO | WO 98/24514 | 6/1998 | | A61N 5/06 |
| WO | WO 98/38933 | 9/1998 | | A61B 17/36 |
| WO | WO 98/51235 | 11/1998 | | A61F 2/00 |
| WO | WO 99/07438 | 2/1999 | | A61F 5/06 |
| WO | WO 99/11324 | 3/1999 | | A61F 5/06 |
| WO | WO 00/54685 | 9/2000 | | A61B 18/20 |
| WO | WO 00/54685 A3 | 9/2000 | | A61B 18/20 |

OTHER PUBLICATIONS

Long-term results after CO2 laser skin resurfacing: a comparison of scanned and pulsed systems; Journal of the American Academy of Dermatology, vol. 37, Issue 5, Nov. 1997, pp. 709-718, E.Victor Ross, Melanie C. Grossman, Daniella Duke and Joop M. Grevelink.*
Heat-induced changes in the mechanics of a collagenous tissue: pseudoelastic behavior at 37 C; Journal of Biomechanics, vol. 31, Issue 3, Dec. 19, 1997, pp. 211-216; S. S. Chen and J. D. Humphrey.*
Jacques "Skin Optics"; Oregon Medical Laser Center News. Jan. 1998; http://omlc.ogi.edu/news/ jan98/skinoptics. html.*
R.M. Adrian, "Treatment of Facial Telangiectasia Using the VersaPulse® Variable Pulse Width Frequency Doubled Neodymium:YAG Laser: A Case Report," 2 pages in length.
J.C. Allain et al., "Isometric Tensions Developed During the Hydrothermal Swelling of Rat Skin," *Connective Tissue Research*, vol. 7, pp. 127-133 (1980).
R.R. Anderson, "Clinical Use of the Lightsheer Diode Laser System," (reprinted with permission from Harvard Medical School, Mar. 1998) from the website located at http://www.lasertraining.com/med-8. htm, printed Sep. 15, 1998, 5 pages long.
R.R. Anderson et al., *International Advances in Surgical Oncology* (vol. 5), section entitled "Lasers in Dermatology Provide a Model for Exposing New Applications in Surgical Oncology," publisher Alan R. Liss, Inc. (1982), pp. 341-358.
R.R. Anderson, Brochure by Palomar Medical Technologies, Inc., "A Clinical Study on Ruby Lasers for Permanent Hair Reduction," 8 pages in length (1999).
R.R. Anderson, "Safety and Efficacy of the Palomar Ruby Laser for Hair Removal," Harvard Medical School, Mar. 1997, 2 pages in length.
R.R. Anderson, "Hair Removal Using Light," Harvard Medical School, Mar. 1997, 2 pages in length.
R.R. Anderson, "Clinical Use of the EpiLaser® System," 8 pages in length (1998).
G.B. Bartley et al., "An Experimental Study to Compare Methods of Eyelash Ablation," Ophthalmology, vol. 94, pp. 1286-1289 (1987).
J.-L. Boulnois, "Photophysical Processes in Recent Medical Laser Developments: a Review," *Lasers in Medical Science*, vol. 1, pp. 47-64 (1986).
Brochure, from Laser Aesthetics, Inc., "The Cool Touch Laser," one page in length.
C. Chess et al., "Cool Laser Optics Treatment of Large Telangiectasia of the Lower Extremities," *J. Dermatol. Surg. Oncol.*, vol. 19, pp. 74-80 (1993).
W.F. Coulson et al., "Nonablative Laser Treatment of Facial Rhytides: Animal Study," *Abstract of BiOS '98 Symposium [Cutaneous Applications of Lasers]*, Jan. 24-30, 1998 in San Jose, CA, one page in length.
C.C. Danielsen, "Age-related thermal stability and susceptibility to proteolysis of rat bone collagen," *Biochem J.*, vol. 272, No. 3, Dec. 15, 1990, pp. 697-701.
C.C. Danielsen, Thermal Stability of Reconstituted Collagen Fibrils, Shrinkage Characteristics upon In Vitro Maturation, *Mechanisms of Ageing and Development*, vol. 15, pp. 269-278 (1981).
J.S. Dover et al., "Pigmented Guinea Pig Skin Irradiated With Q-Switched Ruby Laser Pulses," *Arch. Dermatol.*, vol. 125, Jan. 1989, pp. 43-49.
L.H. Finkelstein et al., "Epilation of Hair-Bearing Urethral Grafts Using the Neodymium:YAG Surgical Laser," *J. Urology*, vol. 146, pp. 840-842 (1991).
R. Fitzpatrick, "Treatment of Wrinkles with the UltraPulse $CO_2$ Laser," 3 pages in length.
L. Goldman, "Comparison of the Biomedical Effects of the Exposure of Human Tissues to Low and High Energy Lasers," *Ann. N.Y. Acad. Sci.*, vol. 122, May 29, 1965, pp. 802-833.
"Laser Surgery of Angiomas with Special Reference to Port-Wine Angiomas,"*AMA Association*, Jun. 18-22, 1967, 8 pages in length.
J.M. Grevelink et al., "Clinical and Histological Responses of Congenital Melanocytic Nevi After Single Treatment With Q-Switched Lasers," *Arch. Dermatol.*, vol. 133, Mar. 1997, pp. 349-353.
M.D. Grossman et al., "Prospective Evaluation of the Argon Laser in the Treatment of Trichiasis," *Ophthalmic Surgery*, vol. 23, pp. 183-187 (1992).
M.D. Grossman et al., "Experimental Comparison of Laser and Cryosurgical Cilia Destruction," *Ophthalmic Surgery*, vol. 23, pp. 179-182 (1992).
K. Kincade, "Demand for Laser Resurfacing Soars," *Dermatology Times*, vol. 16, No. 10, Oct. 1995, 4 pages in length.
P. Kronick et al., "The Locations of Collagens with Different Thermal Stabilities in Fibrils of Bovine Reticular Dermis," *Connective Tissue Research*, vol. 18, pp. 123-134 (1988).
H. Kubota et al., "Atrial Ablation With an IRK-151 Infrared Coagulator," *Ann. Thoracic Surg.*, vol. 66, pp. 95-100 (1998).
J.G. Kuhns et al., "Laser Injury in Skin," *Laboratory Investigations*, vol. 17, No. 1, pp. 1-13 (1967).

(56) References Cited

OTHER PUBLICATIONS

D.B. Kuriloff et al., "Pharyngoesophageal hair growth: The role of laser epilation," *Case Reports*, vol. 98, pp. 342-345 (1988).

J.R. Lloyd et al., "Selective Photothermolysis of the Sebaceous Glands for Acne Treatment," *Lasers in Surgery and Medicine*, vol. 31, pp. 115-120 (2002).

M.A. Mainster, "Ophthalmic applications of infrared lasers—thermal considerations," *Invest. Ophthalmal. Visual Sci.*, vol. 18, No. 4, Apr. 1979, pp. 414-420.

T. Matsumoto et al., "Ruby Laser Treatment of Melanin Pigmented Skin Lesions using Toshiba Model LRT-301A Ruby Laser," *Journal of the Japanese Society for Laser Surgery and Medicine*, vol. 10, No. 3, Dec. 1989, pp. 451-454.

J.B. Murdoch, *Illumination Engineering—From Edison's Lamp to the Laser*, Chapt. 6.8 entitled "Tungsten-Halogen Lamps," published by Macmillan Publishing Company (1985), pp. 208-211.

M.H. Niemz, *Laser-Tissue Interactions Fundamentals and Applications*, Chapt. 3.2.3 entitled "Heat Effects," published by Springer-Verlag Berlin Heidelberg (1996), pp. 77-80.

T. Ohshiro et al., "The Ruby and Argon Lasers in the Treatment of Naevi," *Annals Academy of Medicine*, vol. 12, No. 2 (Suppl.), Apr. 1983, 8 pages in length.

T. Ohshiro, "Treatment by Ruby Laser Beams in the Field of Dermatology," *"Japan Medical News,"* Separate Volume No. 2768, issued on May 14, 1997, 21 pages in length (English translation attached).

H. Ohtsuka et al., "Ru Laser Histological Studies and Clinical Experiences of Ruby Laser Treatment," 9 pages in length (1991) (1st page is an English Abstract).

I. Ono et al., "Histopathological Alteration of Skin and Irradiation of Rudy Laser," *Journal of the Japanese Society for Laser Surgery and Medicine*, vol. 11, No. 4, Mar. 4, 1991, 2 pages in length (1st page is an English abstract).

D.Y. Paithankar et al., "Acne Treatment With a 1,450 nm Wavelength Laser and Cryogen Spray Cooling," *Lasers in Surgery and Medicine*, vol. 31, pp. 106-114 (2002).

J.A. Pearce et al., "Kinetic Models of Laser-Tissue Fusion Processes," *Biomed. Sci. Instrum.*, vol. 29, pp. 355-360 (1993).

L.L. Polla et al., "Melanosomes Are a Primary Target of Q-Switched Ruby Laser Irradiation in Guinea Pig Skin," *The Journal of Investigative Dermatology*, vol. 89, No. 3, Sep. 1987, pp. 281-286.

Press Release, "New Laser Eliminates 'Lipstick Bleed,'" 3 pages in length.

J. Ruiz-Esparza et al., "Nonablative Radiofrequency for Active Acne Vulgaris: The use of Deep Dermal Heat in the Treatment of Moderate to Severe Active Acne Vulgaris (Thermotherapy): A Report of 22 Patients," *Dermatol Surg.*, vol. 29, No. 4, Apr. 2003, pp. 333-339.

Spectrum Medical Technologies, Inc., an operator's manual written by Lasermetrics, Inc., exclusively for Spectrum Medical Technologies, Inc., Q-Switched Ruby Laser System Model RD-1200, 23 pages in length.

E.R. Squibb & Sons, "Lasers Light the Way to New Research Concepts in Science Industry Medicine," 33 pages in length.

R. Tanino et al., "Development of Ruby Laser System for Medical Use," *Journal of the Japanese Society for Laser Surgery and Medicine*, vol. 11, No. 4, Mar. 4, 1991, pp. 93-98.

K. Iwasaki et al., (Astract) "Development of Laser Systems for Treatment of Hyperpigmented Skin Lesions," *Publication unknown—entire article is in Japanese except for the Abstract*, revised Mar. 1, 1989, pp. 26-34 (Abstract appears on p. 34).

Brochure by Palomar EsteLux™, "Pulsed-Light System," website http://www.palmed.com/laser_estelux.html, printed Jul. 15, 2003, 3 pages in length.

Brochure by SCITON, "PROFILE™ Combination Long Pulse Erbium and Long Pulse Nd:YAG 1064," website http://www.sciton.com/public/profile.htm, printed Jul. 15, 2003, 2 pages in length.

Brochure by Lumenis Aesthetic, "VascuLight™ The World's Most Versatile System for Aesthetic Procedures," website http://www.aesthetic.lumenis.com/wt/content/vasculaight, printed Jul. 15, 2003, 2 pages in length.

Brochure by Lumenis, "VASCU*Light*™ ELITE [Versatility and Speed for the Ultimate Aesthetic System]," Copyright 2002, the Lumenis group of companies, 2 pages in length.

Brochure by Lumenis, "VASCU*Light*™ VS [Versatility and Speed for the Ultimate Aesthetic System]," Copyright 2002, the Lumenis group of companies, 2 pages in length.

Brochure by Lumenis, "VASCU*Light*™ SR [Versatility and Speed for the Ultimate Aesthetic System]," Copyright 2002, the Lumenis group of companies, 2 pages in length.

* cited by examiner

US 8,915,906 B2

METHOD FOR TREATMENT OF POST-PARTUM ABDOMINAL SKIN REDUNDANCY OR LAXITY

RELATED APPLICATIONS

The present application is a continuation in part of and claims benefit from U.S. patent Ser. No. 10/996,549, filed Nov. 23, 2004 now U.S. Pat. No. 7,722,600, entitled SYSTEM AND METHOD FOR HEATING SKIN USING LIGHT TO PROVIDE TISSUE TREATMENT, which is incorporated herein by reference, and which is a continuation in part of and claims benefit from U.S. patent application Ser. No. 10/789,139, filed Feb. 27, 2004, entitled SYSTEM AND METHOD FOR HEATING SKIN USING LIGHT TO PROVIDE TISSUE TREATMENT, which is incorporated herein by reference, and the Ser. No. 10/789,139 application claims the benefit of U.S. Provisional Patent Application Ser. No. 60/540,981, filed Jan. 30, 2004, entitled SYSTEM AND METHOD FOR FLEXIBLE ARCHITECTURE FOR DERMATOLOGICAL TREATMENTS UTILIZING MULTIPLE LIGHT SOURCES, AND FILAMENT LIGHT SOURCE TO BE USED IN COMBINATION WITH THE SYSTEM AND METHOD FOR FLEXIBLE ARCHITECTURE FOR DERMATOLOGICAL TREATMENTS, which is incorporated herein by reference, and benefit from U.S. Provisional Patent Application Ser. No. 60/497,745, filed Aug. 25, 2003, entitled OPTICAL DEVICE FOR HEATING SKIN USING NIR LIGHT TO PRODUCE TISSUE SHRINKAGE, which is incorporated herein by reference; and the present application also claims the benefit of U.S. Provisional Application Ser. No. 60/601,352, filed Aug. 13, 2004, entitled METHOD FOR TREATMENT OF POST-PARTUM ABDOMINAL SKIN REDUNDANCY OR LAXITY, which is incorporated herein by reference.

BACKGROUND OF THE INVENTION

In the past various system and methods have been developed for treating different areas of skin with electromagnetic radiation (EMR). Examples of some treatments have been targeted to apply treatment to the skin to achieve hair removal, wrinkle removal, sun spot removal, or to achieve general therapeutic effects. However, in general it has been observed that such application of EMR has not been widely utilized in manner which has been effective to achieve a reduction in, or a tightening of areas of skin where there is a relatively large mass of loose skin. Indeed, in the past this cosmetically undesirable skin condition has been difficult to treat or eliminate through non-invasive medical means. One especially challenging area of lax or redundant skin to treat is post-partum lax, or redundant skin, which can take on the appearance of "baggy", loose, wrinkled, or extra skin, resulting from the simple geometric fact that the abdomen of a pregnant woman undergoes rapid changes in size. Said redundant skin can persist for decades after pregnancy. Indeed, in some circumstances the appearance of the postpartum abdominal skin will become more baggy or wrinkled in appearance a number of years after a pregnancy.

In the past one common method of treating lax post-partum skin has been plastic surgery, such as abdominoplasty which is often a standard invasive medical approach. One advantage of an embodiment of the present system and method is that it provides a non-invasive, low intervention risk, treatment which can be performed in an office setting. The discussion provided below provides for various embodiments of a system and method for using filament light source to provide light, EMR, to provide energy to treat lax, wrinkled, or redundant skin areas. Some specific aspects of treating lax post-partum skin, or other relatively large volume loose skin areas, are discussed in more detail toward the end of the present specification.

DESCRIPTION OF THE INVENTION

One embodiment herein provides a number of advantages over some prior systems, such as no electrical contact with patient and reduced sensitivity to surface hydration, which created in difficulties in some prior systems using RF energy to apply energy to a tissue area being treated. Also using a relatively broadband light source allows for tailored spectral profiles by filtering. Further, an embodiment herein provides for a broadband spectrum light source, which can be driven to output a range of different treatment fluences, and allows for control of the skin temperature to reduce the risk of unwanted thermal injury.

One embodiment of a device herein can use an incandescent lamp with significant optical output in the near-infrared range (NIR) from around 750 nm to 3000 nm. The lamp can be a quartz-tungsten-halogen lamp ("QTH"), but other, longer wavelength lamps may be useful (e.g., ceramic or carbon elements). A housing serves to couple NIR light to skin. The lamp is driven with high current supply, and could potentially utilize a modified version of the high voltage power supply described in the pending patent application filed Jan. 27, 2003 DERMATOLOGICAL TREATMENT FLASHLAMP DEVICE AND METHOD, U.S. application Ser. No. 10/351,981, which is incorporated herein by reference.

Figure 1:
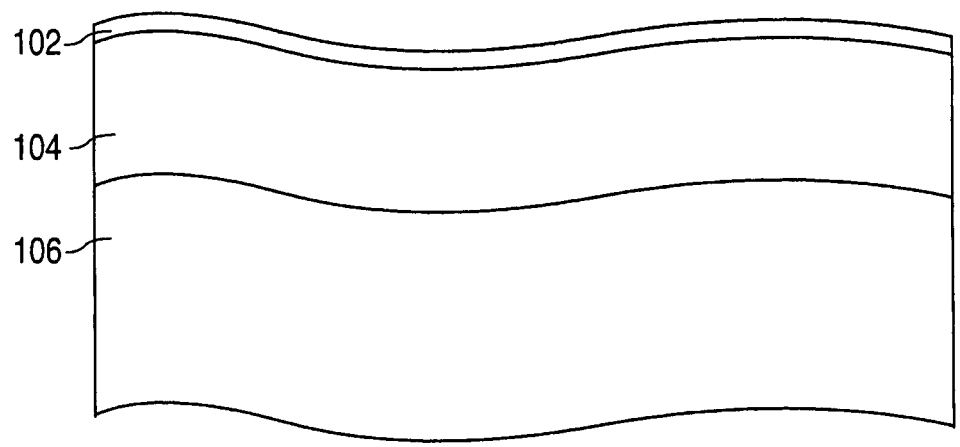
FIG. 1 shows a view of dermatological tissue.

The desired skin absorbance profile is largely determined by water-based absorption in the NIR range, because the dermal layers targeted are generally located 1 to several mm deep. FIG. 1 shows a cross sectional view of dermal tissue, or skin. Layer 102 corresponds to epidermal tissue which has a thickness of approximately 100 μm, and this thickness can vary from patient to patient, and depending on the area of skin being treated. Layer 104 corresponds to the dermal layer which can have a thickness in the range of 1-5 mm, and this thickness can also vary from patient to patient, and depending on the area being treated. One aspect of the treatment herein is to provide for the heating of water molecules in the dermatological tissue being treated. This heating of the water molecules, will in turn heat adjacent tissue and where the temperature of the tissue reaches approximately 50° C. or above, thermal damage to the tissue can be observed. One aspect of the operation of the system and method herein is to heat collagen, which is a protein that makes up much the dermatological tissue, to a temperature in excess of 50° C. One of the effects of sufficiently heating the collagen, is to cause the collagen to change its characteristics as a result of thermal damage. This changing of the collagen characteristics is sometimes referred to as a shrinkage of the collagen, or remodeling, and this shrinkage of the collagen, can result in the reduction of wrinkles, or what appears to be a general tightening of the skin, in the area where the collagen has been sufficiently heated.

In general, different effects of due to collagen shrinkage can be achieved by controlling the temperature profile in tissue being treated. In some circumstances a treatment may target both relatively shallow skin tissue, including possibly tissue in the epidermal layer, and to also heat deeper tissue in the dermal layer. In some other circumstances the treatment can be targeted at heating the dermal layer in the range of 1-6 mm, while minimizing the heating the upper dermal layer and the epidermal layer. Regardless of the specific treatment, it is generally desired to provide for some relatively deep tissue heating in the dermal layer.

To produce deep tissue heating and potential remodeling, or collagen shrinkage, a relatively large volume of skin must be heated. Associated thermal relaxation times are measured in 100s to 1000s of milliseconds, and in some cases in 10s of seconds. Existing art using lamps to heat skin is largely limited to volumes relaxation times below 1000 ms. Thermal relaxation time for deep bulk skin heating will allow exposures>1 second, in general to deposit sufficient NIR energy. Thus, as recognized herein a device may then be turned on for as long as several seconds to produce the desired thermal profile, said profile is based on the knowledge that tissue held at temperatures above 50° C., and preferably above 60° C., for any significant length of time will experience thermal damage, and in the case of collagen this thermal damage can result in remodeling or shrinkage.

A simple calculation provides a rough illustration of the heating required to produce collagen-changing temperatures. For this calculation consider a cylindrical slug of water 3 mm thick and 6 mm diameter and having a thermal relaxation time of approximately 10 seconds. So, heating such a volume could happen more or less adiabatically in a second. If the goal is to pre-heat skin (water) by 20 C in this time, this volume of water (approximately 0.1 cm3) would require (20 C)(4 J/C*cm3)(0.1 cm3)=approx. 8 J. That is 8 J/1 sec=8 watts. Assume the electrical to delivered optical efficiency of the light source is 5%, then 160 watts of electrical power is required. To obtain good electrical to optical efficiency, the source in one embodiment is smaller in its dimensions (e.g., width) than the treatment spot size (which is approximately 6 mm in diameter for purposes of this sample calculation). If the optical source is an incandescent filament, it would then ideally have a minimum electrical rating of at least 200 watts and be only a few mm in size.

In one embodiment, a source delivering peak powers in the NIR between 10 and 100 W per $cm^2$ would be required. Many generally available 600-1000 W quartz-tungsten-halogen lamps operated at rated power are unlikely to be useful as direct sources, since typical power densities at the lamp envelope are on the order of ~1000 W/20 $cm^2$=50 W/$cm^2$, with the power density or irradiance falling rapidly with distance. The NIR portion of this results in power-in-band densities at the envelope in the low 10's of W/$cm^2$. Getting higher power densities can be achieved through utilization of different possible techniques. One possibility is using a filament light source for a limited life of operation and overdriving the filament lamp. Another option, which could be used alone or in conjunction with overdriving the filament lamp is collecting the output light from the entire envelope filament lamp and directing it to skin by means a reflector. Another option which could be used in combination with the above options, or alone, is employing water cooling of the quartz envelope of the lamp to enable the use of smaller lamp envelops.

Light sources other than filament light sources could also be used, but one of the challenges is finding an economical light source that outputs light of spectrum which is useful for heating water, or more specifically for outputting light across desired parts of the NIR range. For example, it is known that Nd:YAG laser light penetrates too deeply to effectively heat water in skin at appropriate depths to perform skin remodeling. The effective penetration depth is a function of the reduced scattering coefficient and the absorption strength of (mainly) water in skin. It is desirable to use somewhat more shallow penetrating light by seeking a waveband in which absorption is somewhat stronger than 1064 nm in water and in which scattering is no greater than the 1064 nm wavelength in skin. Light falling between 950 and 1400 nm has an absorption depth in water that varies between 1 and 28 mm. Taking into account scattering in a simple model, the effective penetration of NIR light in skin in this wavelength range varies from approximately 0.3 to 2.0 mm. Filtering the NIR light produced by a filament lamp can result in an effective penetration depth (function of scattering length and absorption depth) that can be tailored to aid in creating a desired thermal depth profile in tissue being treated. However, no matter what the spectral shape may be, the light intensity in tissue, and the absorption and temperature profiles can only have a shape that is a sum of decaying exponential curves, since the absorption characteristic of each wavelength in skin follows a Beer's Law like profile. The consequence is that the thermal profile has the same basic shape, and that the spectral profile (absent any geometric shaping of the optical field, such as focusing) can only alter the general depth and strength of a Beer's Law-like thermal profile.

Useful bands for providing thermal remodeling can include 1150-1400 nm, and perhaps 1500-1850 nm, and in fact light up to 3000 nm range can be beneficial. In the former, scattering is somewhat reduced with respect to 1064 nm light in water, and the absorption depth in water is deep to moderate, ranging from 4-12 mm. Considering the optical penetration depth that applies in skin, including the effects of scattering, the actual depth of penetration is approximately 3 mm.

In the latter range, scattering is significantly reduced compared to 1064 nm in water, and the absorption depth is relatively shallow (1-2 mm). Between these two spectral ranges, light from 1350-1550 nm is strongly absorbed and will generally contribute to relatively shallow epidermal heating.

In one mode of treatment the desired result is to produce higher temperatures in deeper thermal layers relative to the temperature at the epidermis. Heat is primarily deposited in a Beer's Law type profile, which subsequently transfers heat to the bulk of the skin. Absent some cooling applied to the surface of the skin, the application of light energy would create a temperature generally be higher in the epidermis than in the dermis.

Figure 2A:
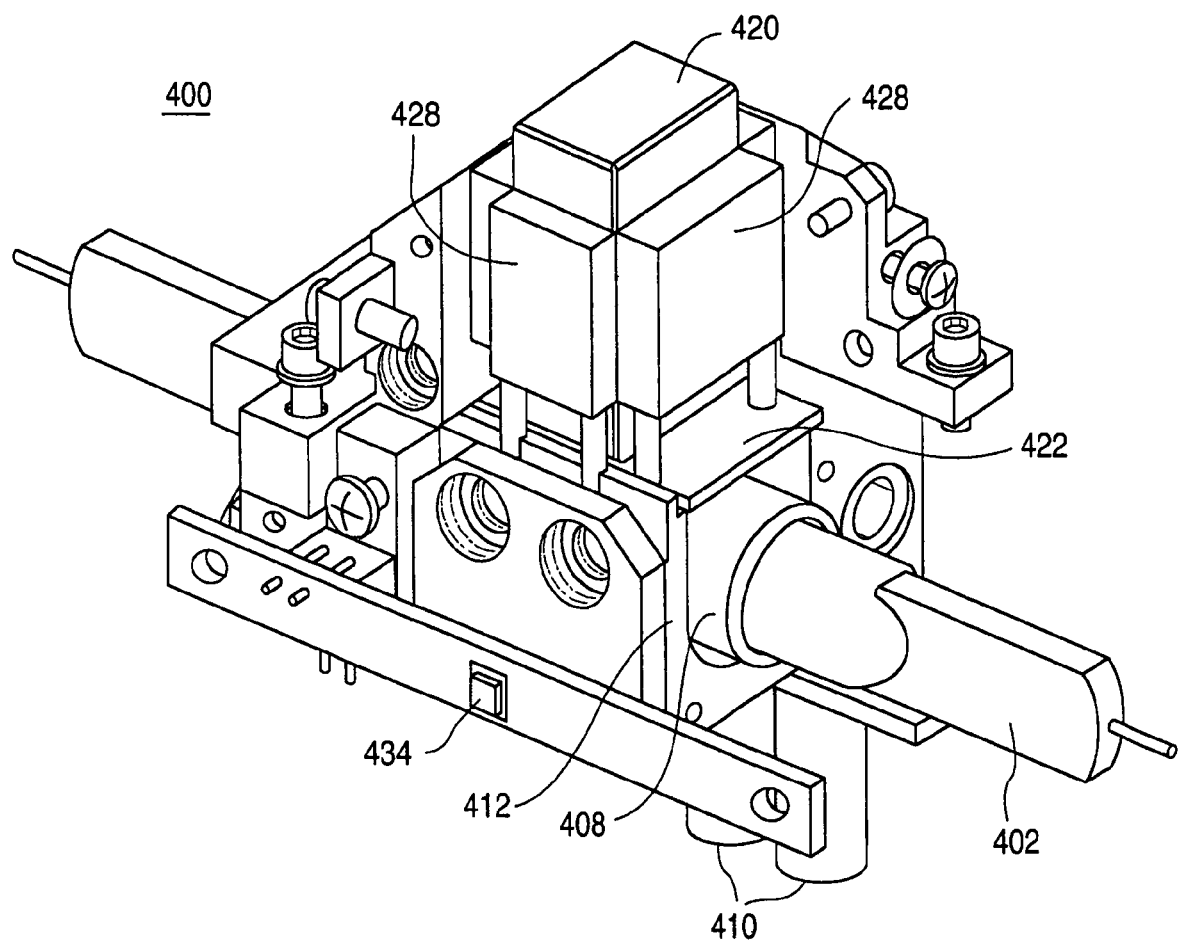
FIGS. 2a-2b show views of an embodiment of a system herein.
Figure 2B:
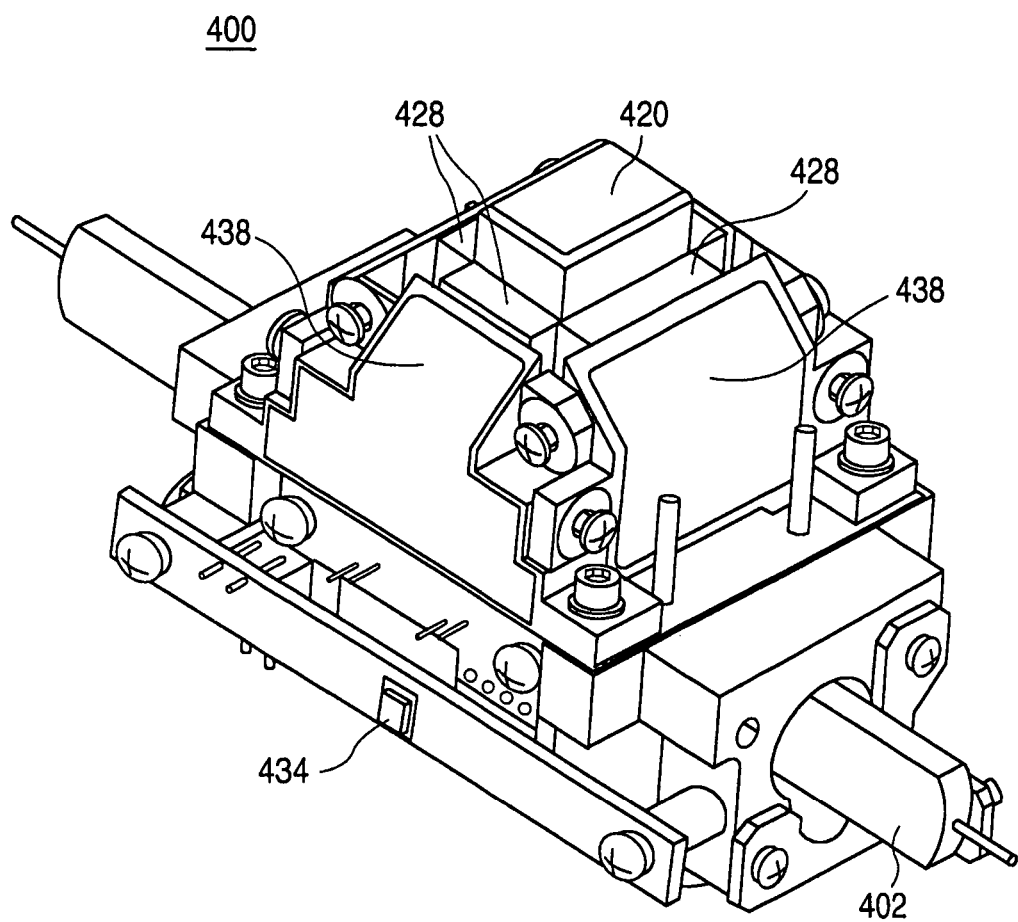
Figure 3A:
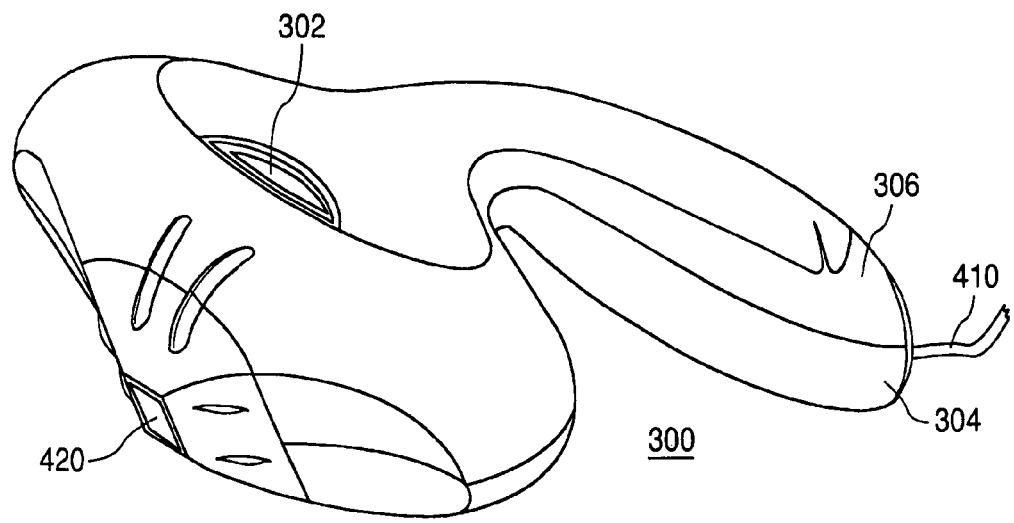
FIGS. 3a-3b show views of an embodiment of handpiece of a system herein.
Figure 3B:
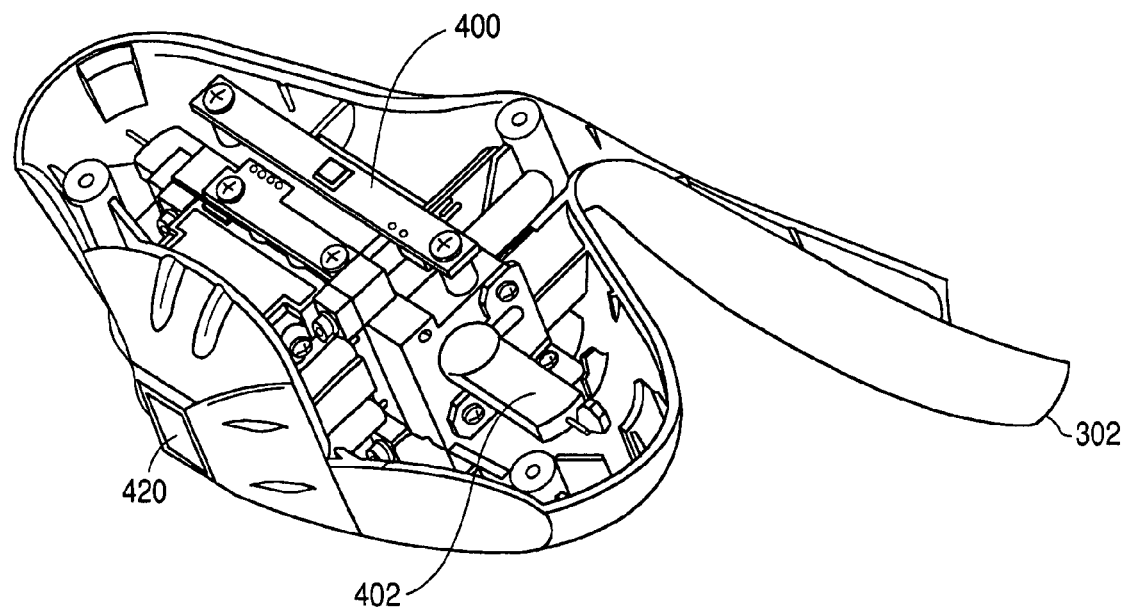
Figure 4:
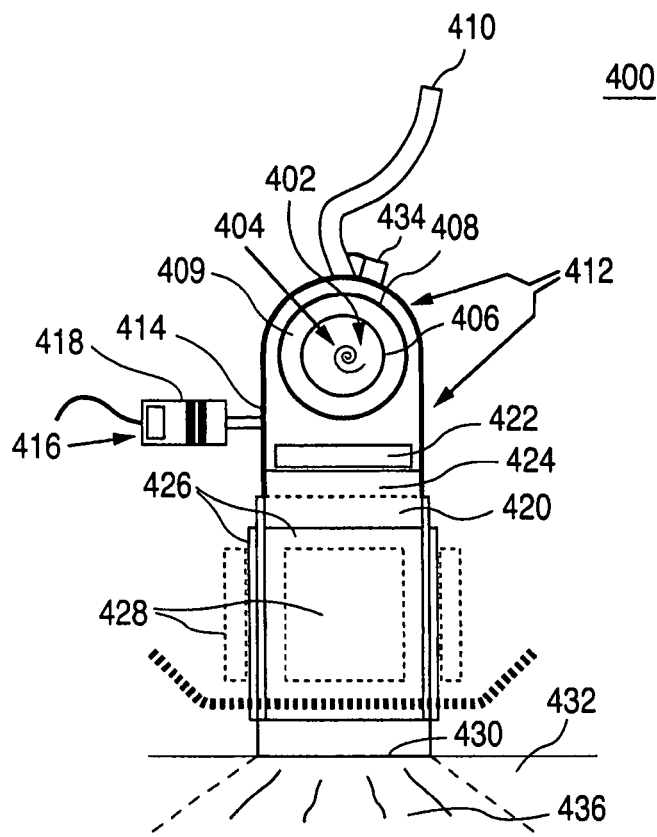
FIG. 4 shows a cutaway view of an embodiment of a system herein.

FIGS. 2a-2b and FIG. 4 illustrates aspects of a filament lamp system 400 of an embodiment herein which can be used to deliver NIR light to tissue to provide treatment exposures. FIG. 3 shows an ergonomic handpiece 300 in which the filament lamp system 400 is disposed. FIG. 2a shows a view of the filament lamp system 400 with some of the elements removed so as to be able to view elements in the system 400. FIG. 2b shows a view of an assembled filament lamp system which would be disposed in the handpiece 300. In reviewing the FIGS. 2-4, common reference numbers have been used to identify elements, where the same element is shown in various views represented by the figures. FIG. 4 shows a simplified cutaway view of the filament lamp system corresponding to FIG. 2a. The function of the filament lamp system is described in detail in connection with FIG. 4 below. However, a brief discussion of FIGS. 2a-2b, and FIGS. 3a-3b is provided initially to give an overview of the system.

FIG. 2a shows the system 400. The system 400 includes a filament lamp 402, and surrounding the filament lamp is a flow tube 408. A housing is 412 is provided, and light from the filament light is transmitted through other optical components such as a filter 422 and a sapphire block 420. The sapphire block 420 is cooled using thermoelectric coolers 428. The system also includes an LED 434 to indicate when tissue is being treated. FIG. 2b corresponds to FIG. 2a, but shows additional copper cooling blocks 438 secured against the thermoelectric coolers 428. These cooling blocks 438 can be supplied with cooling fluid, which operates to dissipate heat generated on the outer walls of the thermoelectric coolers 428.

FIGS. 3a-3b illustrate an embodiment of an ergonomic handpiece 300 with the filament light system disposed therein. The handpiece can consist of molded plastic pieces, or other suitable material. As shown the handpiece 300 has two molded plastic pieces 304 and 306. A cavity is formed between the molded plastic pieces, and the filament lamp system 400 is disposed in this cavity. Two apertures are providing the handpiece. One aperture is covered with a lens 302 through with light from the LED 434 is transmitted. The second aperture allows the sapphire block 420 to protrude from the handpiece so that it can be pressed against the skin. Epoxy can be applied to the seam between molded plastic pieces and the sapphire block to improve the seal between the sapphire and the plastic.

FIG. 4 shows a simplified cut away view of the system. The system includes a filament lamp 402. This filament incandescent lamp is an incandescent light source, and includes a filament 404. The filament lamp includes a quartz tube 406 in which a gas is disposed. In one embodiment the quartz tube 406 has a diameter of 10 mm. The length of the filament itself is approximately 22 mm, while the overall length of the lamp is approximately 4 inches. In order to obtain the desired light output the filament can be of a diameter of approximately 0.75 mm, and formed in to a helical shape having approximately 7 turns. The quartz tube 406 of the filament lamp is disposed within a flow tube 408 which can be formed with a transparent material such as glass or Pyrex. A fluid such as water is disposed within the cooling annular region 409 between the flow tube 408 and the quartz tube 406. This water can pumped through the annular flow region 409 by a pump and cooling system. In one embodiment the diameter of the flow tube 408 is 11 mm. Thus, the annular flow region 409 provides a spacing of approximately 0.5 mm between the outer wall of the quartz tube 406 and the inner wall of the flow tube 408. The water disposed in the flow region 409 can serve two purposes. One purpose is to cool the filament lamp. Given the relatively high power of the lamp, in one embodiment the filament lamp has an electrical rating of 400 W, and the small diameter of the lamp, and the confined geometry of the handpiece, traditional air cooling of the filament lamp is not possible. A second function of the water is to filter out some of the wavelengths of light generated by the filament lamp (through absorption). The amount of light filtered can be varied by providing flow tubes 408 with different diameters. In one embodiment different interchangeable handpieces could be provided where the systems disposed in the handpieces provide different thickness for the water envelop in the annular flow region 409. As the thickness of the water, which forms an envelop around the lamp is increased, the light transmitted through water will be subject to more absorption in the water, and thus less of the light at wavelengths which are absorbed by water will be transmitted through the flow tube 409. An umbilical connector 410 will transmit electrical power and coolant fluid to the system 400.

The filament lamp and the flow tube are disposed in a housing 412. The housing can be formed of a metal such as aluminum. The inner wall of the of the housing can be coated with a highly reflective metal, or it could be highly polished aluminum. In one embodiment a highly reflective gold coating is provided, where gold is used because it is highly reflective for NIR light. The housing is provided with a small aperture 414 which allows for a photodetector 416 to be disposed such that it can sense the light output power transmitted by through the flow tube 408. Depending on the sensitivity of the photodetector, and the output power, the photodetector can be provided with an attenuator 418. The reflective housing is coupled to a sapphire block 420. A filter 422 can be provided such that additional undesired light can be filtered out prior to transmitting light from the reflective housing 412 into the sapphire block 420. In one embodiment the filter 422 is a non absorbing NIR and IR transmitting wavelength filter. The interface between the filter 422 and the sapphire block 420 is provided with an antireflecting coating 424 on the surface of the sapphire block to minimize power loss which can occur as light is transmitted through the filter 422 into the sapphire block. The lateral sides of the sapphire block 420 can be coated with metal surfaces 426. These metal surfaces should be as reflective as possible to minimize losses as the light is transmitted through the sapphire block. It should be recognized that an embodiment of the system might be implemented without the metal coating on the sides, and the total internal reflection of the sapphire block could suffice, so long as other elements were not in direct contact with the sapphire block. In one embodiment the metal used is Aluminum, as this metal has reasonably good reflective properties and easily adheres to the surface of the sapphire block. A cooling system is provided to control the temperature of the sapphire block, and the system can use thermoelectric coolers disposed on the metal surfaces 426. These thermoelectric coolers 428 operate to control the temperature of the sapphire block 420. The operation of thermoelectric coolers, which is known in the art, is such that by application of the electrical current to the thermoelectric cooler, one side of the thermoelectric cooler can be made cooler, while the other side of the thermoelectric cooler becomes hotter forming an electrically driven heat pump. In the embodiment shown, the cool side of the thermoelectric cooler is adjacent to the sapphire block. Additionally, although not shown in FIG. 4, cooling fluid can be used to remove heat from the side of the cooler which is not adjacent to the sapphire block 420. The sapphire block could be replaced with a block of different material, which would form a lightwave guide. Sapphire is, however, a desirable material for the system as it is a good transmitter of light, and it is also a good conductor for heat. In operation the outer surface 430 of the sapphire block is pressed against the area of the patient's skin 432 which is to be treated. The light 436 from the filament lamp is then transmitted into the patient's skin.

Figure 10:
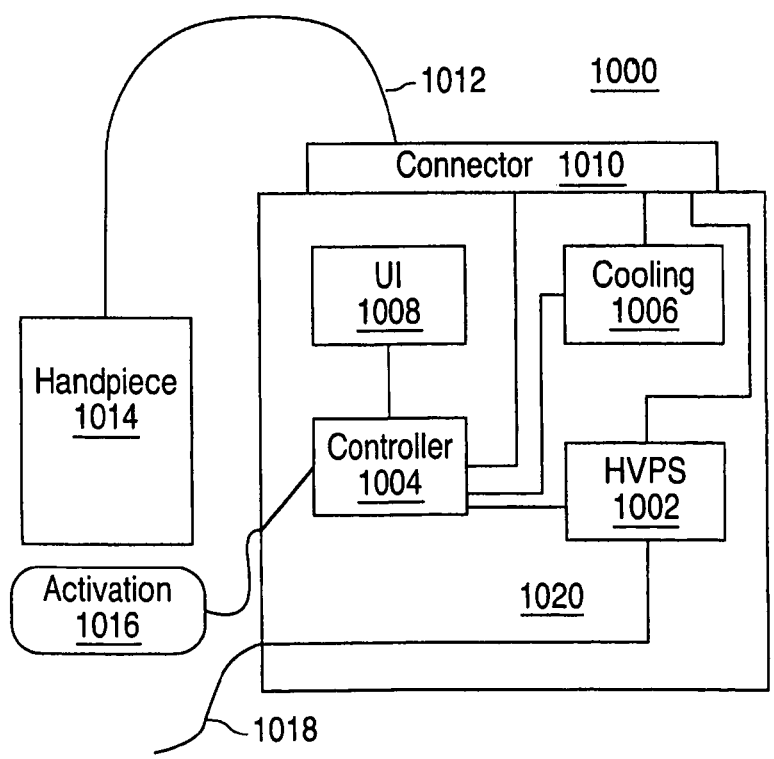
FIG. 10 illustrates an embodiment of a system herein.

As discussed above the umbilical cable connects to the lamp system to provide control signals, electrical power and cooling fluid to the system 400. FIG. 10 provides a view of an embodiment of a system 1000 herein. As shown the system 1000 includes a main console 1020. Although the main console is shown as a single unit, it could in fact be multiple components connected together. The main console includes a controller 1004 which controls the overall operation of the other components of the system 1000. A power cord 1018 is provided to receive AC power, a power supply which can include a high voltage power supply (HVPS) 1002 for driving the filament lamp, provides power to elements of the system 1000. The main console also includes a user interface. In one embodiment this user interface 1008 is a touch screen display, and the controller is operable to drive the user interface 1008 to display different screens where a user can input treatment parameters. A cooling system which controls the temperature and flow of fluids which are used to control the temperature of components in the hand piece 1014. The power for driving the flashlamp, control signals and cooling fluids are delivered to the hand piece via the umbilical cable 1012. The umbilical cable is connected to the main console via a 1010. This connector, can include multiple connectors to allow for multiple hand pieces to be connected to the main console at different times. The controller operates to recognize the handpiece which is selected by a user, and to provide appropriate user interfaces and controls the selected hand piece which is being used to apply a treatment. An activation switch 1016 such as a foot pedal is provided so that a user can initiate the driving of the light source by stepping on the foot pedal.

Figure 5:
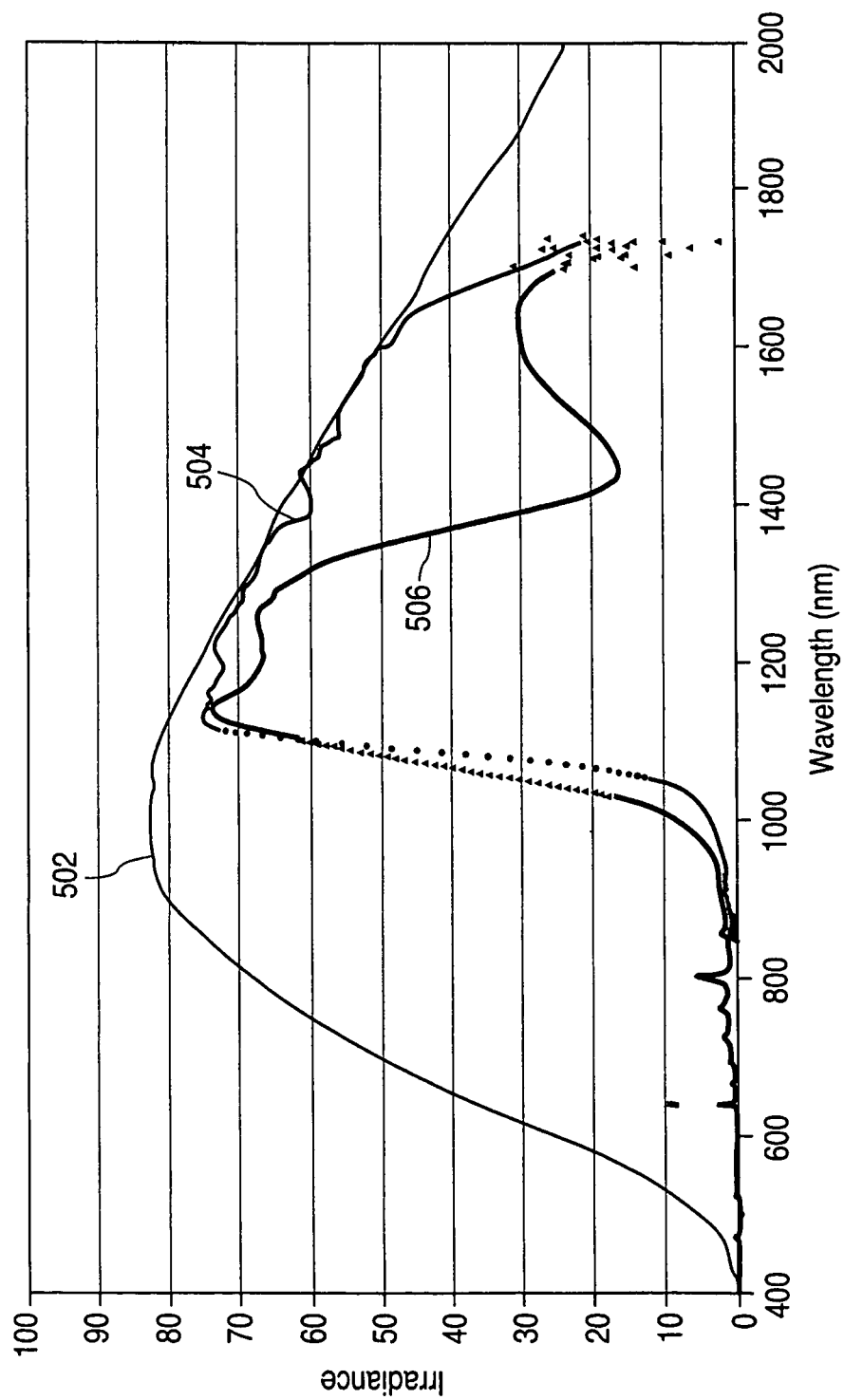
FIG. 5 shows a graph illustrating filtering of a broadband spectrum, according to an embodiment herein.

FIG. 5 illustrates aspects of the operation of the system 400. The trace 502 shows an approximation of optical spectral power which is generated by the filament lamp without any filtering. As is known a quartz-tungsten-halogen filament lamp outputs a broad light spectrum approximating a black body radiation. By using a relatively heavy gauge tungsten filament the amount of NIR light for a fixed input power can be increased over thinner gauge filaments. This is because the temperature that the radiating filament operates at for the input power is lower for larger gauge wires, and as is known the radiation temperature determines in large part the spectral curve. In order to achieve relatively deep dermal heating, for example, up to approximately 4-6 mm, without damaging or burning the more shallow epidermal layers of the skin it is advantageous to filter out wavelengths of the spectrum which could be absorbed by more shallow layers of skin. The filter 422 operates to filter out light in the spectrum below approximately 1050 nm. The trace 504 shows the effect of filter 422 on the light generated by the filament lamp. It should be noted that the rapid fall off of the power in trace 504 at approximately 1750 nm, is not in fact due to the filter 422, rather it is a limitation of the IR detector array used to measure the power output the filament lamp and in reality trace 504 would approximate the upper end of the trace 502. Trace 506 shows the irradiance of the light output where the filter 422 is filtering light below 1050 nm, and the water in flow tube is operating to filter out some of the light which is strongly absorbed by water. At approximately 1450 nm, where water absorption coefficient of water is very strong, it can be observed that a large amount of the irradiance from the lamp is filtered out. It should be noted the shown rapid fall off of trace 506 at approximately 1750 nm is due in large part to the limitations detector used to measure the power, and in fact a more gradual decrease in the power would be present above 1750 nm. Depending on the desired treatment, systems providing for a thicker or narrower water envelop around the quartz tube of the filament lamp can be used. Where heating of shallower layers of the dermis, or possible parts of the epidermis is desired the thickness of the water envelop can be reduced by, for example, using a smaller diameter flow tube. This will result in less absorption, or filtration of light by the coolant water in the range of 1450 nm, and this light energy which is not filtered would then be absorbed in the shallower layers of the dermis and the epidermal layer. Where deeper heating is desired, then it can be beneficial to increase the absorption of the light in the range of 1450 nm to reduce the absorption of this energy in the shallower layers in the skin. This allows for ability to keep the more shallow layers of the skin relatively cool, in part by reducing the light energy which would be absorbed in the more shallow layers of tissue. This reduction of the light which would be absorbed in the more shallow layers, and the cooling of the sapphire window to dissipate heat in the shallow layers of the dermis and epidermis, while still providing light energy that will propagate to deeper layers of the dermis, enhances the desired result of heating the deeper layers of tissue relative to more shallow layers of tissue.

Figure 6:
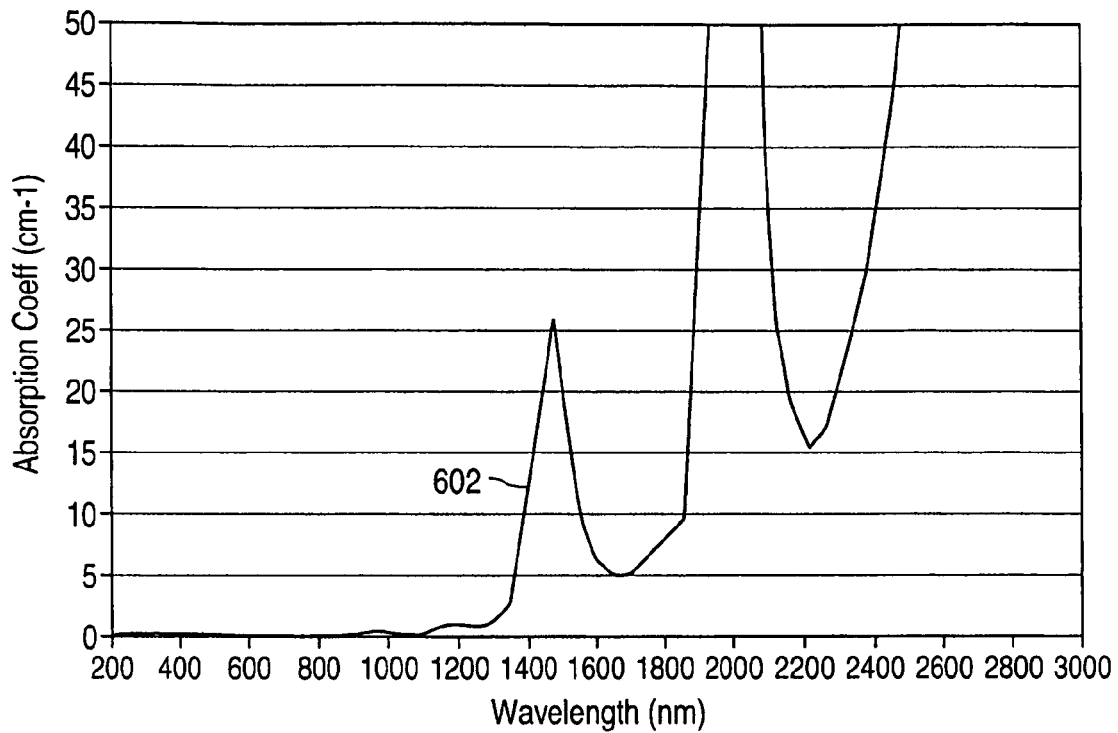
FIG. 6 is a graph illustrating the absorption coefficient of water.
Figure 7:
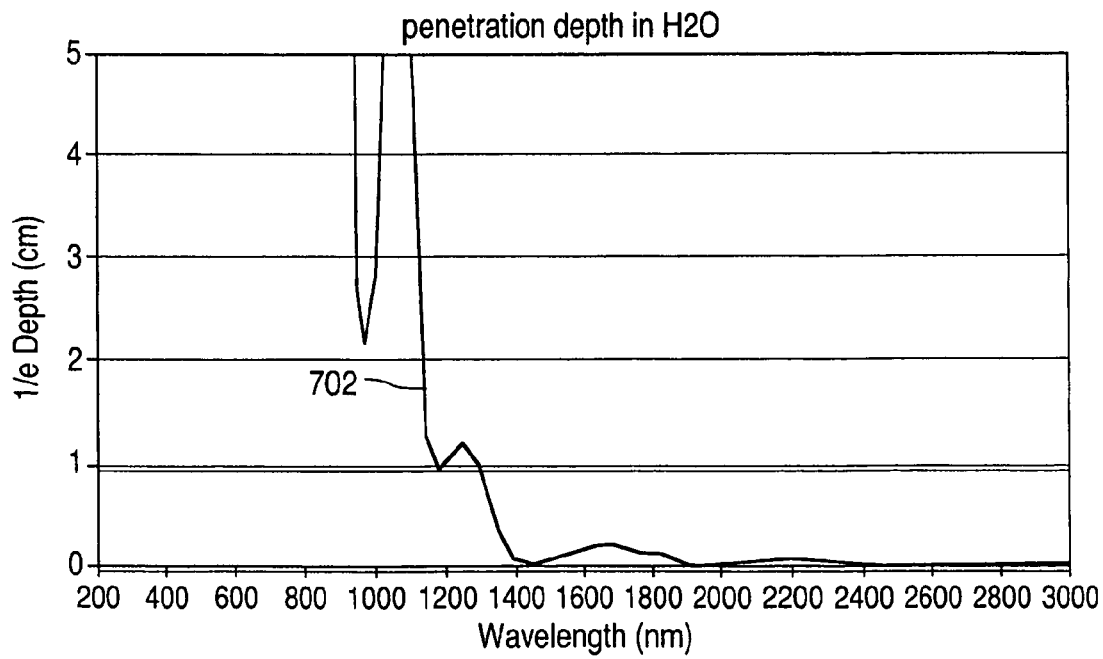
FIG. 7 shows a graph illustrating the penetration of different wavelengths of light in water.

FIG. 6 shows a graph with a trace 602 showing the absorption coefficient of water. As would be expected based on the discussion of FIG. 5, water has as very strong absorption coefficient at approximately 1450 nm. FIG. 7 shows a trace 702 that corresponds to the depth of light penetration into water. This graph illustrates that by filtering out light in the range of 1450 nm and at wavelengths above 1850 nm much of the energy which would be absorbed by the water in the shallow layers of the dermis or epidermis is be removed.

Figure 8:
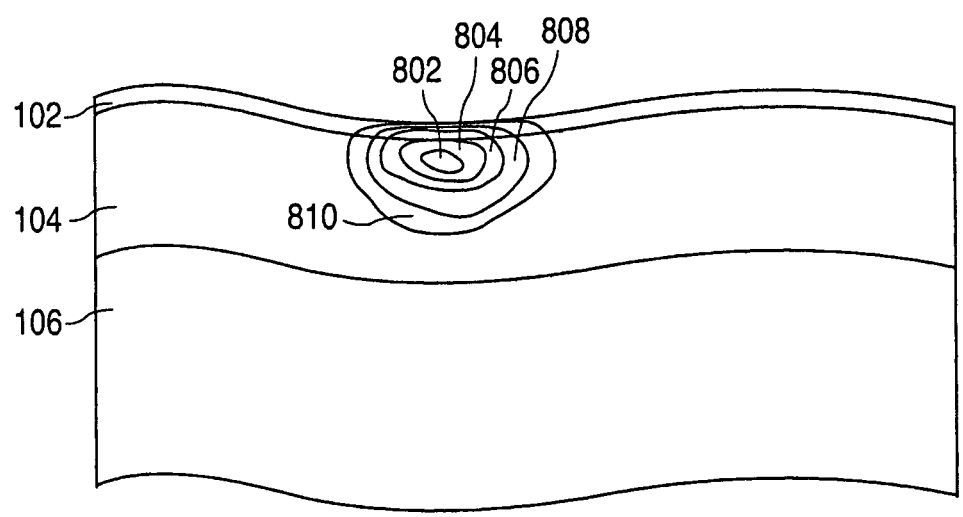
FIG. 8 illustrates an example of a thermal profile in tissue being treated.

FIG. 8 shows an idealized view of the temperature profile in dermatological tissue where an exposure treatment has been applied using a system and method herein. The goal of one treatment herein is to provide for heating in regions 802 and 804 to approximately 60° C. while regions 806 and 808 and 810 remain at much cooler temperatures due to the active cooling of the sapphire block and the filtering out of light which would be absorbed in the shallow layers of the dermis and epidermis. In one mode of treatment regions 802 and 804 would be in the depth range relative to the top surface of the tissue of approximately 1-4 mm.

To achieve the type of tissue heating described above consideration must be given to the temperature of the sapphire block and the driving of the filament lamp. When a user has activated the filament hand piece, by for example stepping on the activation switch 1016, the controller and power supply coupled to the filament lamp hand piece by the umbilical cable are activated to provide a treatment. In one embodiment the user will be able select an amount of fluence for a treatment exposure using the user interface 1008. Once the user has selected an amount of fluence, the controller will determine how long the filament light source will be activated to generate light to output the desired fluence. The system is designed to provide a fluence range of from 10 J/cm2 to 50 J/cm2. Of course these amounts could be modified if desired. Once the user has selected the desired amount of fluence, the hand piece 1014 is positioned so that the sapphire window is against the area of skin to which the exposure is to be applied. The user can then step on an activation pedal which will cause the treatment to begin. Upon stepping on the activation pedal, an LED 434 will light to indicate that the treatment has begun and that the user should not remove, or move, the handpiece and sapphire window relative to the area of patient's skin being treated. Initially, the system will operate to apply electrical current to the thermoelectric coolers and the temperature of the sapphire block will be brought to a treatment temperature. In one embodiment the treatment temperature is 20° C., but this could be set to a different temperature. The cooled sapphire block will continue to be pressed against the patient's skin for the initial cooling period where the sapphire will operate to cool the surface of the patient's skin. In one embodiment this initial cooling period will last for period of approximately 1 second. After approximately 1 second the power supply will operate to provide electrical energy to the filament of the filament lamp for a period of time until the desired fluence as been delivered to the patient's tissue. Depending on the desired fluence light will be transmitted from the filament to the patient's skin for a period of time ranging from slightly more than 1 second, an appropriate minimum could be for example around 1.2 seconds, and an appropriate maximum could be around 5 seconds. As will be discussed in more detail below, the power supply will stop applying electrical current approximately 1 second prior to the end of the treatment exposure and the hot filament will continue to emit light until it has cooled sufficiently. The amount of time for which the filament radiates after current application is stopped depends on the thermal mass of the filament and the operating filament temperature, and can range form 0.1 to 2 seconds. During the application of the light from the filament lamp, the cooling system, including the thermoelectric coolers, will continue to cool the sapphire block, ideally keeping the temperature at the initial treatment temperature. After the filament light has stopped outputting the treatment exposure, the cooling system will continue to cool the sapphire block for a post treatment exposure time period, and the sapphire block will operate to dissipate heat from the patient's skin. The LED 434 will remain lit through the initial cooling time, the time when the treatment exposure is being applied, and through the post cooling time period. By keeping the LED lit, the user will know not to remove the hand piece and the sapphire block until the treatment exposure has concluded, and the post cooling time period has ended. In addition to the LED turning off to signal the end of a treatment, an audible signal could be provide to indicate to user that a treatment has been completed.

FIG. 9 shows an example of the current and voltage that could be used in driving the filament lamp. In driving the filament lamp, pulses of electrical current are used to drive the filament of the filament lamp. FIG. 9 shows the current output for driving a filament light source, and the corresponding power output 910 detected by the photodetector which senses the power in the housing. In this example a filament light source would be driven with an initial pulse 908 of electrical current having duration of 100 ms, and a current amplitude of 50 A, and then subsequent pulses 902 and 904 of electrical current. Depending on the desired operation of the system pulse widths of a wide range of different widths could be used, and the frequency of the pulses could be increased or decreased. The long initial pulse 908 is used to initially heat the filament light source, and rather than using one relatively long pulse a series of shorter closely spaced pulses could be used. Pulses 902 show 0.5 ms pulses and 904 shows a 1 ms pulse, the duration between pulses can be varied based on a signal from a photodetector which senses the optical output power, and/or based on a voltage sensed across the lamp. In one embodiment for example the applied electrical pulse would be such the output of power from the filament light would be ±1.5% of 16 watts. Thus, when the photodetector sensed that the power output has dropped to a threshold level a 0.5 ms pulse of 50 A would then be applied to the filament light source. As shown in FIG. 9 each pulse of current would result in a corresponding voltage applied to the filament light source. The system can operate such that toward the end of a 0.5 ms pulse, based on a sensed optical output power, or a sensed voltage across the lamp, a subsequent 0.5 ms pulse can be applied if the optical power or voltage has not reached some threshold value. Voltage pulse 914 and current pulse 904 illustrate a situation where two 0.5 ms pulses are applied to form a single 1.0 ms pulse. Of course a wide range of different approaches could be used to drive the filament lamp to output the desired power. The output power from the filament light source is shown in FIG. 9 as detected by a photodetector in curve 910. The area 912 is a break in the time line, during which additional pulses would continue to be applied to the filament light source. The operation of the filament light source is such that it will continue to output electromagnetic energy for so long as the filament remains sufficiently hot. Thus, the curve 910 shows that optical power continues to be output by the filament light source even after the pulses of electrical current are no longer being supplied to the filament light source. In the example, shown in FIG. 9 for example where the last electrical pulse is applied at 2.5 seconds, the filament light source would continue to output a significant amount of output power up to about 3.4 seconds.

The filament can also be driven continuously by a supply, it is not a requirement to pulse the filament current at intervals during the treatment. This was actually a method developed to obtain filament capability using the same power supply that drives flashlamps. Other variations and different methods could be utilized such as providing a higher current during the preheat phase of the pulse, in order to bring the lamp up to heat quickly. This could be combined into one long pulse with higher current in the beginning and lower current at the end. An alternate control method would be to control the voltage applied to the lamp. The voltage would ramp up at a controlled rate to limit the inrush current. Alternately the voltage control would be a step voltage applied and the current limit of the supply would limit the current.

The above described operation of the power supply driving a filament light source, illustrates an aspect of an embodiment of the present system. Specifically, a filament light source is normally considered to be a relatively low current, low voltage device. However, the filament light source can be driven with the same power supply which is used to supply high current and high voltage that is required to drive a flashlamp. As describe above the ability to control the power supply to short pulses of relatively high current, allows for the controllable power supply to drive the filament light source in a manner for providing effective treatments.

In another embodiment of the system herein, the filament lamp could be driven with lower current power supply which would apply a more continuous, but lower amplitude current to drive the filament. As one skilled in the art will recognize a variety of different power supplies could be used to drive the filament lamp.

Figure 11:
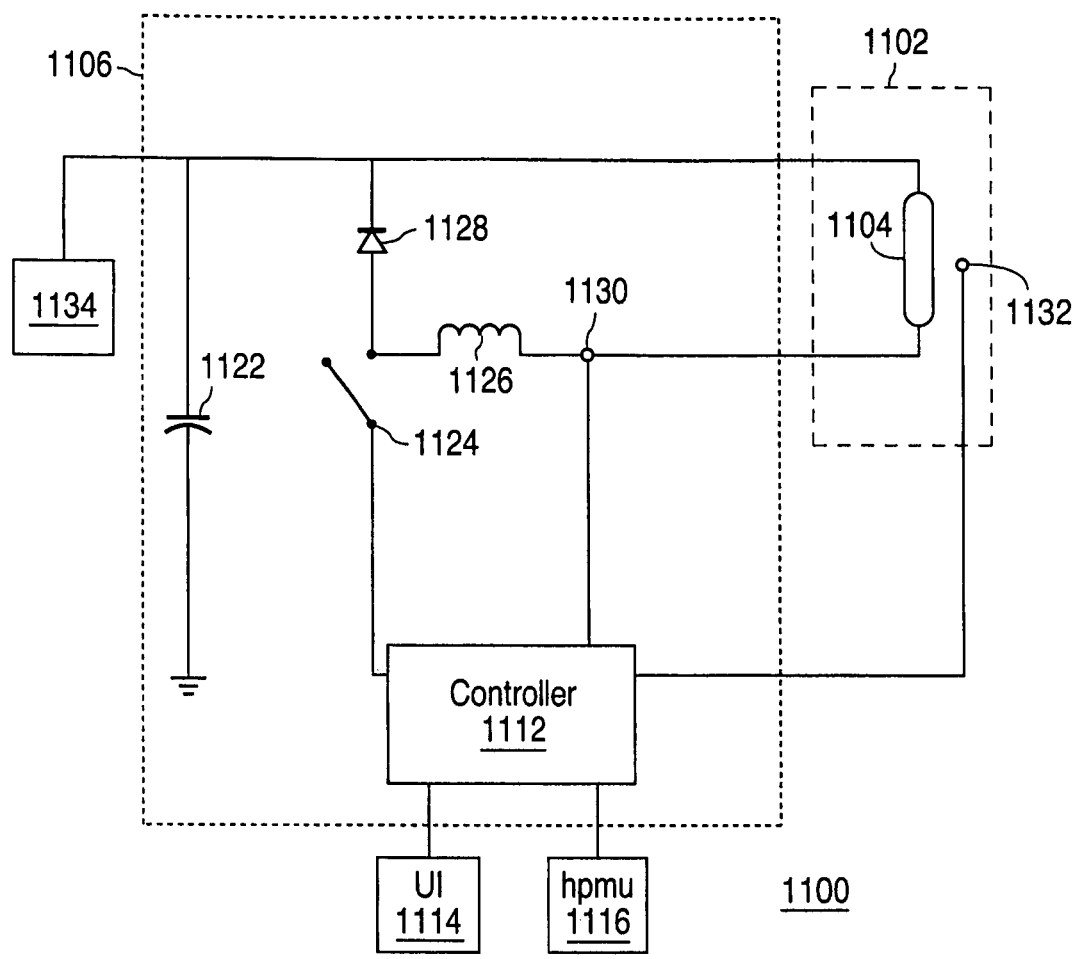
FIG. 11 shows an embodiment of a system herein.

FIG. 11 shows a detailed view of an embodiment of system herein. Specifically, FIG. 11 shows a view of a high voltage power supply 1106 which could be used to drive the filament lamp 1104 in the handpiece 1102 in the manner described above in connection with FIG. 9. As shown in detail in the U.S. Provisional Application Ser. No. 60/540,981, filed Jan. 30, 2004, entitled SYSTEM AND METHOD FOR FLEXIBLE ARCHITECTURE FOR DERMATOLOGICAL TREATMENTS UTILIZING MULTIPLE LIGHT SOURCES, AND FILAMENT LIGHT SOURCE TO BE USED IN COMBINATION WITH THE SYSTEM AND METHOD FOR FLEXIBLE ARCHITECTURE FOR DERMATOLOGICAL TREATMENTS, which is incorporated herein by reference, the power supply is very controllable and can operate to switch between and drive different types of light sources. In one embodiment the power supply uses a controlled chopper circuit with an inductive filter element 1126, operating in a pulse width modulated controlled current mode (in which the current is controlled and the voltage is determined by the device impedance and the impedance of the filter). Power supply 1106 could be also operated in a pulse width modulated controlled voltage mode (in which the voltage is controlled and the current is not controlled) or in a controlled power mode (in which the voltage and/or current are controlled in a manner resulting in controlled power).

In an embodiment herein, the controller of the power supply 1112 receives signals originating from the user interface 1114 and possibly sensors in the hand piece management unit which can determine when the handpiece 1102 has been removed from a seated position, and based on these signals determines how to drive the filament lamp when the user activates the filament lamp, by stepping on a foot pedal switch for example.

The operation of the power supply will be described in the context of the situation where a user has removed the handpiece 1102 from a hand piece management unit, and initiated the activation of the filament lamp 1104 of the hand piece 1102. In this situation when the hand piece 1102 is removed from a resting or seated position and activated the filament lamp, the operation described above will be performed.

The energy storage capacitor 1122 is charged by the main electrical supply 1134 to a level allowing the desired energy to be delivered without unacceptable lamp voltage droop, when driving the filament lamp at the desired current. When switch 1124 is closed current ramps up current through the filament lamp 1104, inductor 1126, and switch 1124. When the appropriate output power or current is reached, the controller 1112 opens the switch 1124 and the current now diverts to the diode 1128. When the current flow or output power drops to an appropriate level the controller 1112 again turns on the switch 1124 and the cycle repeats until a pulse is complete.

This toggling of switch 1124 on and off during a treatment exposure results from the photodiode 1132, or use of a voltage sensing circuit, determining that the optical power has reached a maximum value, and in response the controller opens the switch, and when the optical power drops to a low target level the switch closes, which increase the current through the filament lamp. It should be noted that as discussed in connection with FIG. 9, one embodiment operates with a central target for optical power of around 16 W. However, the power supply operation could be adapted such that the power supply drove the filament to output both varying amounts of power and varying treatment exposures. Also the current sensor 1130 and photodiode 1132 can be used independently, or in concert to control the optical power delivered to skin.

Figure 12:
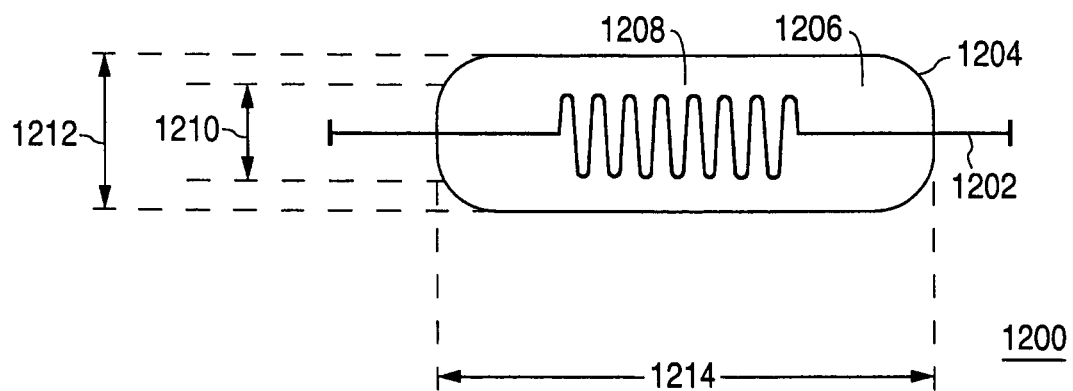
FIG. 12 shows an embodiment of a filament lamp of the present system.

FIG. 12 shows an embodiment of lamp herein 1200. Aspects of suitable QTH lamps are described above. As discussed above it is important to be able to obtain sufficient optical power from the lamp in order to obtain the desired heating. Many previously available filament lamps are of relatively large dimensions relative to a treatment exposure area, and it can be very difficult to utilize these previous designs to obtain the desired heating. To achieve higher power the dimensions of a filament lamp in an embodiment herein have been changed relative to previously available lamps. The elements of a lamp 1200 illustrated in FIG. 12 illustrate significant dimensions of the lamp. The lamp includes a tungsten filament 1202. A portion of the filament 1202 is disposed in a quartz tube 1204, and the area inside the tube is filled with a gas 1206 which can include halogen. The portions of the filament that are outside of the tube 1204 can be partially sealed in tabs of the quartz tube which are not shown, and these tabs could be used to physically and electrically couple lamp 1200 with the other elements of the system. In one embodiment the length of the tube 1204 is about 2.4 inches (60 mm). In one embodiment the diameter of the filament is 0.75 mm, but a range of different thicknesses could be used. A center portion 1208 of the filament 1202 is formed in to a helical coil shape. In one embodiment the helical coil shape has a diameter 1210 which is approximately 6 mm. In one embodiment the tube diameter 1212 is approximately 10 mm. The ratio of the diameter of the tube 1204 and the diameter of the helical coil 1208 is 10:6. This ratio is very different that previous filament lamps where a ration of greater than 10:1 is very common. Generally, filament lamps utilize air-cooling. Where air cooling is used it is important to maintain a sufficient area for cooling the lamp, and generally one way of ensuring sufficient area is to maintain relatively large tube diameter relative to the diameter of the coil. Generally as the ratio of the tube diameter to the helical diameter gets below about 5:1 it is believed that air cooling will no longer be sufficient to cool the lamp, when it is driven at currents which are necessary to output the optical power required for the thermal treatments described herein, and as the ratio becomes less (for example the 2:1) as is the case described in connection with the lamp 1200 shown in FIG. 12 the cooling issues must be addressed, and the required energy fluences are obtained.

In some potential embodiments, where the diameter of the tube is relatively close to the diameter of coil, when a given the amount of current is used to generate a treatment exposure, traditional air cooling may not be sufficient to keep the lamp cool enough so that it will not become damaged and fail. Thus, the flow tube and liquid cooling discussed above can be utilized to cool the lamp.

It should be recognized that the filament light source discussed herein is advantageous over some other light sources in that it is relatively inexpensive, and outputs a broad spectrum of light in the NIR range. At present flashlamps do not appear to provide as good a source for producing a broad range of power in the NIR spectrum, but some flashlamps might be suitable to produce such a range of light, and could be considered for use in a system for providing deep thermal heating.

As discussed above, some embodiments herein provide a method which uses externally applied electromagnetic radiation to produce heating for a controlled amount of time in skin. The thermal profile created by an embodiment of a system herein is such that the epidermal temperature is lower than the dermal temperature (e.g., shallower layers of skin are cooler than portions of the deeper layers of skin). This thermal profile provides a thermal gradient with a continuous variation in temperature as a function of skin depth, in which the superficial layers of the epidermis and dermis are at lower temperatures than portions of the deeper dermis. The epidermal temperature is held to a safe level while the dermis is heated by the electromagnetic (EM) radiation. It should be noted that EM radiation includes a wide range of different wavelengths of energy which can range from very short wavelengths, such as optical energy, to much longer wavelengths in the RF range.

In one embodiment optimal heating is produced through control of the absorption depth profile associated with the penetration of the applied EM radiation to the skin. The temperature profile, and its duration, affect the lax skin in such a way as to reduce, or reduce the appearance of, or otherwise tighten the appearance of, the excess skin. Desired depth profiles produce significant temperature rises in the range of 1 and 5 millimeters.

In one embodiment peak dermal temperatures are at least 40 C, with practical ranges falling between 40 and 70 C, and duration of the EM exposure ranges from 1 to 20 seconds. The time and temperature history during the exposure determines the degree to which redundant skin is effected, and therefore the degree of reduction, or the appearance of reduction of the redundant skin.

The depth of dermal heating is determined by the penetration of the applied infrared radiation, and generally not by thermal diffusion, because the optical penetration depth significantly exceeds the thermal diffusion length; or put another way, the time of exposure to EM, while relatively long and measured in seconds, is still short compared to the thermal relaxation time of the absorbing tissue volume. The depths of heating in the skin are measured in mm, while the lateral extent of the heating in the skin is largely determined by the footprint, or area, of the contact waveguide/light channel which is delivering the treatment energy to the skin.

Penetration of NIR optical radiation is determined in large part by the wavelength filtering. In one embodiment treatments can be performed with filtering that is bounded on the short wavelength side by a 1050 nm long wave pass filter, and by the cooling water annulus having optical thickness of approximately 0.5 mm, where the water annulus strongly attenuates NIR radiation between 1400 and 1550 nm, and beyond 1850 nm.

For example in one embodiment the treatment footprint, or output area of the sapphire block 420, measures 10×15 mm. With the filtering and this treatment spot size, maintaining the area of the sapphire block which is in contact with the treatment area at 20° C. provides adequate epidermal safety/protection for a wide range of treatment fluences.

In some embodiments treatments can be applied without pain management (without need for pain killers) and such treatments can be applied in a stamping mode, with the contact area of the sapphire block held in contact with skin through a single exposure cycle (pre-cool, exposure, optical "cool-down", post-cool). Where in one embodiment the pre-cool would be achieved by placing the cooled sapphire window in contact with an upper surface of the tissue being treated; the exposure is achieved by driving a filament lamp with electrical current; the optical cool down occurs when the optical energy decreases as a result of stopping the electrical current being applied to the filament; and the post-cool down is achieved by keeping the cooled sapphire block in contact with the tissue.

Treatments can be performed on all flat, or low curvature, portions of the face (forehead, temples, cheeks, neck). Additionally, as discussed in more detail below, treatments can be applied to relatively high volume areas of loose or baggy skin, such as on post-partum abdominal skin. Care should be taken on high curvature portions of the face (mandibular line, nose, ocular orbit) because where the contact surface is rigid contact cooling is more difficult to achieve when the targeted treatment area is curved and rigid. In such areas consideration should be given to avoiding treating such an area, or a contoured contact surface or other cooling means should be used to cool the skin.

Without pain management or medication, patients can be treated with fluences at or near 32 $J/cm^2$. Typically, such treatments consist of one complete "pass", or at most two, where a pass consists of covering the entire area to be treated with single adjacent exposures. In one embodiment, mild pain management is utilized with sedatives, such as Vicodin or Valium, in combination with analgesic pain relievers (such as non-steroidal anti-inflammatory drugs (NSAIDs) like ibuprofen) and more aggressive treatment parameters are used. In some cases alternative pain medicine may be considered for use in place of NSAIDs, because for some treatments, the anti-inflammatory effect of NSAIDs may undermine treatment efficacy. In one embodiment as many as 4 four passes are used with each application of energy, or pass, providing in the range of 40-45 $J/cm^2$. It should also be noted that different fluences can be used for skin on different parts of the body. For example, skin on the forehead and temple areas, can be treated with less fluence than areas of skin on the neck.

In one embodiment single exposure durations can range from 1 to 10 seconds. For the nominal delivered optical power of approximately 10 $W/cm^2$, exposures are typically between 3 and 5 seconds. Time constants associated with the volume treated in one exposure are many seconds. If adjacent areas are treated consecutively, thermal build-up may produce unintended high temperatures. It therefore may be desirable to treat an entire contiguous area by means of applying exposures to non-adjacent positions, returning to fill in untreated areas. Alternatively, separating adjacent exposures by lateral distances of a few millimeters will allow thermal zones to have minimal overlap and avoid over-temperature/over-exposure. More aggressive treatments may proceed by intentionally overlapping consecutive treatment sites in such a way as to build up subsurface temperatures. Thermal relaxation times of the treated tissue are in the range of 1 to many seconds, so that the interval between successively applied treatment sites is sufficiently short that the tissue temperature rise persists long enough that the temperature can be increased at depth by applying overlapping treatments.

Alternative treatments may use lower fluences and many exposures. Examples might include from 2-10 passes at a fluence tolerable without pain management; such a fluence could be at or below 32 $J/cm^2$.

Tailored Thermal Exposures and Thermal Injury

In one embodiment herein, an aspect of the treatment is to create thermal tissue damage or injury from the delivered infrared exposure. However, it can be advantageous to deliver the infrared exposure in a controlled manner. Thermal tissue damage is generally a function of the time-temperature history of the tissue.

In the theory of selective photothermolysis (SPT), the pulse duration of the applied radiation and the characteristic thermal relaxation of the target tissue determines the target tissue temperature-time history, and the associated thermal injury. For some treatment applications a general principle is that for effective tissue damage, without collateral damage to surrounding tissue, the pulse width of the applied radiation should be on the order of, or shorter than, the target absorbing structure's thermal relaxation time (defined as the characteristic time for the temperature difference between the structure or volume and its surroundings to decrease by a significant amount). In some applications where the pulse time is in this range, then the pulse width time can be used to estimate the temperature rise of the target tissue as an adiabatic temperature rise due to the heat generated by direct absorption of the applied radiation by the target.

An embodiment of the present invention utilizes an approach which is somewhat different than SPT, in that it delivers energy which results in general heating of volume of tissue, and is not particularly selective so as to provide for treating primarily a targeted structure in a volume or area of tissue. Where considering volume heating, tissue damage may be described as occurring through an arbitrary temperature-time history experienced by the particular volume of tissue. In one treatment of thermal tissue damage (See, e.g., Markolf H. Neimz, "Laser-Tissue Interactions, Fundamentals and Applications" pp 78-80, Springer-Verlag Berlin Heidelberg (1996) which is incorporated herein by reference) the degree of cell or tissue damage is represented by a normalized Arrhenius time-temperature integral that varies between 0 and 1:

$$C_{damage}[t]=1-\exp[A\int\exp(-\Delta E/RT)^* dt]$$

The degree of thermal injury to tissue can be produced by any number of thermal histories, represented by a time dependent temperature function T=T(t). The temperature function T is in turn determined by the applied radiation intensity, the absorption characteristics of the target (and surrounding) tissue, and the thermal diffusion and transport character of the target and surrounding tissue.

U.S. Pat. No. 5,885,274, entitled Filament Lamp for Dermatological Treatment, describes using an energy source to produce a thermal injury in skin by employing transient temperature spikes (one or more) that are short compared to the thermal relaxation time. In U.S. Pat. No. 5,885,274, infrared light from a filament lamp is used to produce temperature spikes in skin that may be relatively short. In an embodiment of system, such short period pulses would also produce rapid dermal temperature spikes, followed by a relatively long interval during which the temperature slowly decreases. Since the Arrhenius integral is exponentially dependent upon temperature, it could be problematic to create a measured dose of thermal injury in this way, particularly since the size of the temperature spikes may vary or may not be easily measured.

In one embodiment herein when a target amount of thermal injury is desired in a large tissue volume, the system operates to produce a relatively small temperature rise for a relatively long period of time. In some applications an embodiment herein can operate to control the temperature in such a way as to produce a constant temperature over the exposure duration by varying the applied radiation power appropriately. In this way, a desired level of thermal injury can be produced using lower peak temperatures, and use of longer lower temperature pulses is generally more controllable than shorter, higher temperature exposures.

In general, it may be advantageous to control temporal changes in the applied radiation intensity on time scales shorter than, comparable to, and even longer than, the target tissue volume thermal relaxation time. Having arbitrary control over the applied radiation intensity as a function of time allows for control of the thermal injury. This may also be used advantageously for pain management.

Operation of an embodiment herein has shown that a fixed applied radiation power for a duration of time resulted in steadily rising temperatures throughout the treated volume, where the treatment volume corresponded to a relatively large volume of skin. This is because the thermal relaxation time of the target volume is large, on the order of 10 seconds, so that even many seconds of exposure results in a continuously increasing temperature profile 1302 over time in the tissue area being treated (see FIG. 13A). The result is that the thermal damage is increasing with time, potentially rapidly as the Arrhenius damage integral depends exponentially on temperature. Additionally, the level of pain increases sharply as the temperature crescendos at the end of the exposure.

Figure 13A:
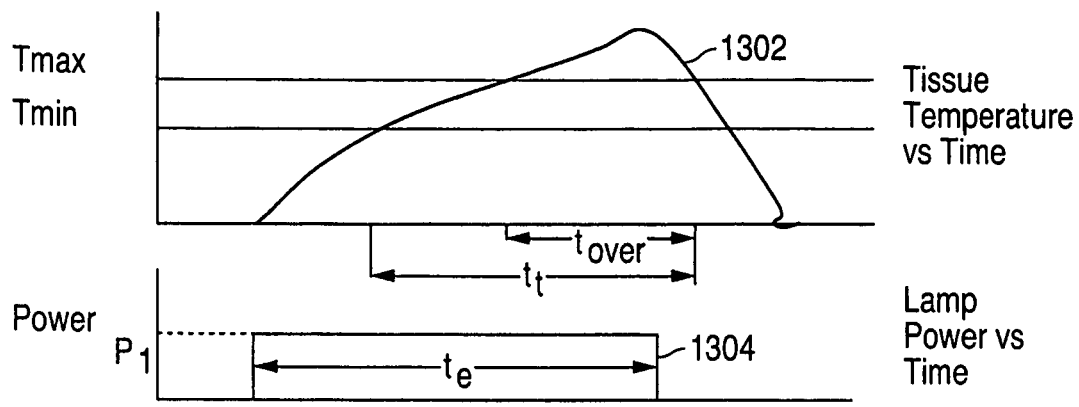
FIG. 13A-D illustrate an embodiment with tailoring of thermal exposures through peak optical power control in one embodiment herein.

In FIG. 13A applied EM power 1304, which could be EM power from a filament lamp, and the subsequent heating profile 1302 of a volume of tissue are shown. In this initial simple case, the applied EM power is fixed at a constant level of $P_1$ for an exposure time $t_e$. The temperature of the tissue volume rises above a minimum therapeutic temperature $T_{min}$ and past the ideal upper therapeutic limit of $T_{max}$. The duration of time at which the tissue is exposed to temperatures above the minimum therapeutic temperature $(T_{min})$ is the treatment duration, designated as $t_t$. The tissue is then exposed to undesirably high temperatures for some duration, said time designated as $t_{over}$. Typical treatment parameters for skin tightening treatments in this mode are: $T_{max}$=65 C, $T_{min}$=55 C, $t_e$=3 sec, $t_t$=1.5 sec, $t_{over}$=0.5 sec, $P_1$=25 W (17.7 W/cm$^2$.) Note that in the example considered herein the area of where EM energy is applied to the skin is 1.5 cm$^2$; which results in a power density of 25 W/1.5 cm$^2$ which gives a power density of 17.7 W/cm$^2$.

Figure 13B:
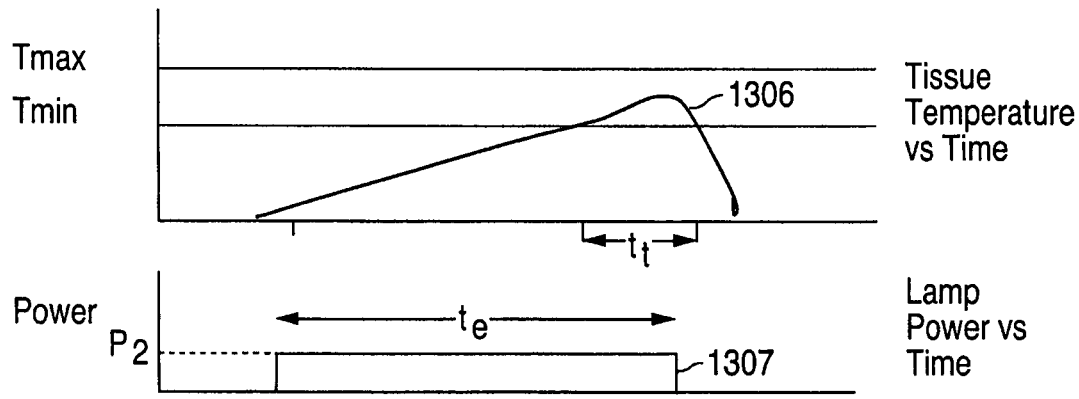

In order to avoid overheating, the power applied $P_2$ 1307, as shown in FIG. 13B, is decreased to avoid a temperature rise past the desired maximum temperature $T_{max}$ (see FIG. 13B), the result is a temperature profile 1306 which provides a potential under-treatment, with the time-temperature integral and tissue damage being smaller than desired.

Applying a constant lower optical power 1307 avoids exceeding desired temperature treatment, but limits the time-temperature integral by reducing the total time, $t_t$, that the tissue is above the therapeutic threshold, $T_{min}$. A typical example would use: $T_{max}$=65 C, $T_{min}$=55 C, $t_e$=4 sec, $t_t$=1 sec, $t_{over}$=0 sec, P2=16 W (10.7 W/cm$^2$.)

An embodiment herein provides for producing the desired thermal effects, but with less pain during treatments, by appropriate design of the applied radiation temporal profile. In order to achieve the desired thermal injury without excessively overshooting the targeted maximum temperatures, and thereby potentially exceeding acceptable pain thresholds, an embodiment herein provides for control over the applied radiation temporal profile.

Figure 13C:
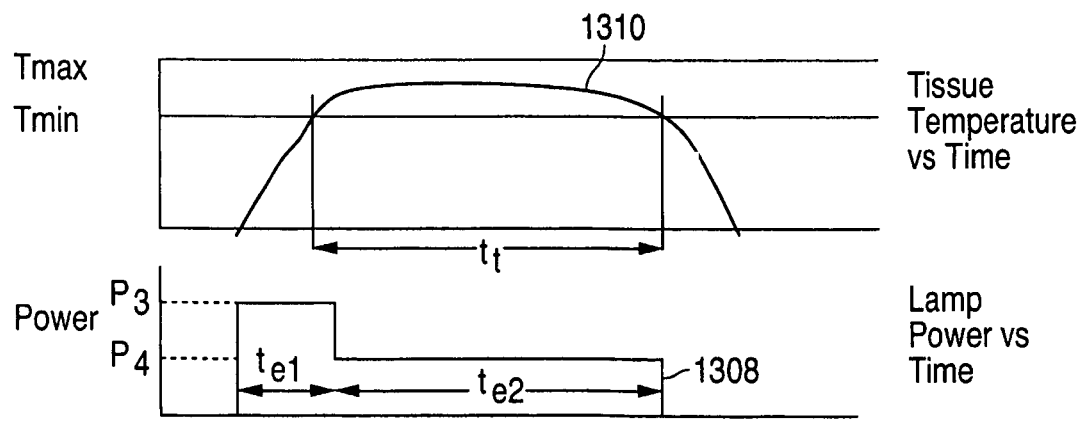

In one embodiment of the present invention, the closed loop optical power control was used to provide a two level power exposure profile 1308 in FIG. 13C. The profile 1308 shows the power output from the energy source. The higher initial power of profile 1308 causes the temperature profile 1310 for the tissue being treated to reach the desired target temperature rapidly. Subsequently, the power in profile 1308 is decreased to a value sufficient to maintain the desired temperature in the temperature profile 1310 for a desired amount of time, where the desired treatment temperature is in a temperature range between $T_{max}$ and $T_{min}$ and the desired temperature range could in one embodiment be significantly narrower than $T_{max}$ and $T_{min}$.

FIG. 13C shows a 2-level optical power profile 1308 applied to produce a relatively uniform temperature 1310 in the target tissue volume. A first EM power of P3 is applied for an initial time $t_{e1}$, followed by a reduced power of P4 applied for a time $t_{e2}$ where $t_{e2}$ can correspond to a temperature treatment maintenance time period. The initially larger P3 raises the tissue temperature to the desired treatment temperature in therapeutic band between $T_{min}$ and $T_{max}$. The subsequent lower P4 maintains the tissue temperature in the treatment temperature range in the therapeutic temperature band. Typical 2-level parameters can be in the range of approximately: $t_{e1}$=1 sec, P3=25 W (17.7 W/cm$^2$), $t_{e2}$=2.5 sec, P4=12 (8 W/cm$^2$), $t_r$=3 sec. Given current lamp technology and general treatment parameters most time values for maintaining the treatment temperature in the volume of tissue being treated will be at least 1.2 seconds, and typically will be 2 seconds or more.

Figure 13D:
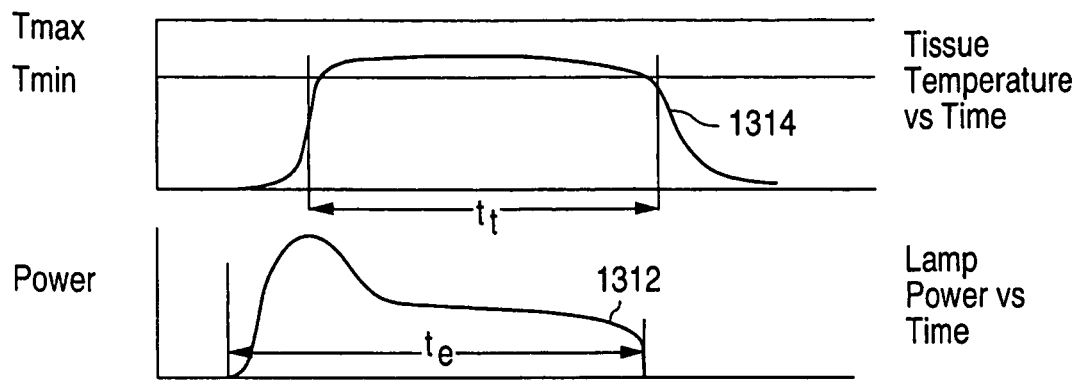

In one embodiment an ideal radiation temporal profile would have the applied power initially high, and then continuously and smoothly decrease the power toward a constant level that would maintain the tissue temperature at a fixed value, or a value in a therapeutic range between $T_{min}$ and $T_{max}$. FIG. 13D illustrates operation of an embodiment herein where the applied power pulse 1312 is continuously and smoothly modified to achieve a temperature profile in the targeted treatment tissue at a therapeutic level between $T_{max}$ and $T_{min}$. While the applied power 1312 is shown as being continuously and smoothly changing during the time $t_e$, the same effect could be achieve where power of the power pulse is adjusted to apply a discrete, but relatively small changes in the applied power where the small changes in the applied power are implemented over relatively short time intervals so that the applied power will approximate a smooth and continuously changing power profile as shown in trace 1312.

Figure 16:
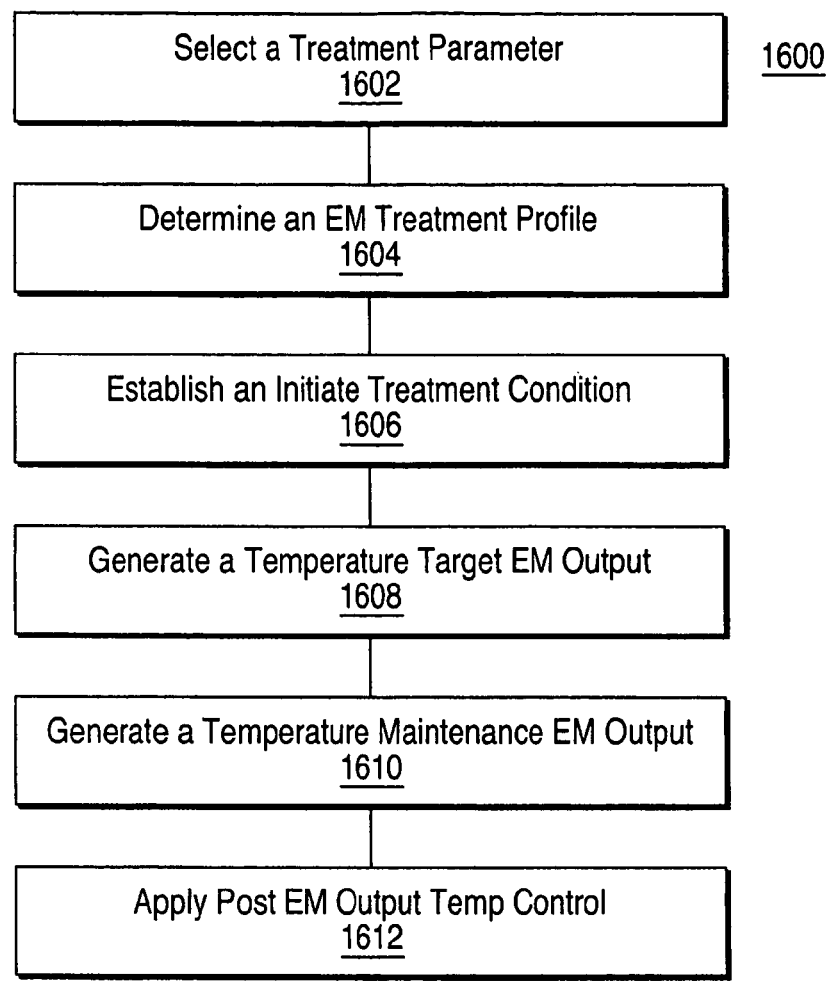
FIG. 16 shows an embodiment of a method herein for applying a therapeutic treatment.

FIG. 16 shows an embodiment of a method 1600 herein. Initially a user who is applying a treatment to a target area can select a treatment parameter, and this could include selection of multiple different parameters. For example, for a treatment area which has a large amount of relatively thick lax skin a user might select a relatively high treatment setting. The user could be presented with a menu via the user interface 1008 of FIG. 10 which allows a user to select a total amount of energy to be applied, or a target temperature, or a length of pulse etc. In one embodiment a user could be presented with an option of merely selecting a level of treatment, where a level of treatment might very from 1 to 10 with 10 being the highest energy level for a treatment. Based on a user selected treatment parameter, the controller could refer to a look up table, or other data form which provides for an electromagnetic output profile, such as shown in FIGS. 13A-13D. Based on the selected treatment parameter the controller determines an EM treatment profile 1604. The sapphire block can be used to apply cooling to the treatment area to establish an initial treatment condition 1606. In one embodiment the initial treatment condition could be for example using the sapphire block in contact with the treatment area to bring the surface area of the treatment area to approximately 20 C. Based on the determined EM treatment profile, the controller would then drive the EM source, for example the filament lamp, to output an initial portion of the EM treatment exposure. In one embodiment this initial portion of the EM treatment exposure would be a temperature target EM output which operates to bring the treatment area to a desired treatment temperature in a range between Tmax and Tmin. After generating the initial portion of the EM treatment exposure, the output of the EM source is reduced to generate 1608 a treatment temperature maintenance EM output, where, as described above, this is generally a reduced EM output relative to the initial portion of the EM treatment exposure. As described above, the level of the power of the EM exposure output could be changed smoothly and continuously, or it could be changed over different time levels to different specific power outputs. After conclusion of the EM treatment exposure the method could further include applying a post EM output temp control to the treatment area.

For example, the sapphire block 420 of the system could be kept in contact with the treatment area to lower the temperature of the treatment area after the EM exposure.

It should be recognized that while the power levels discussed above in connection with FIGS. 13A-13D are in the 10s of watts/cm$^2$ and higher, or lower power levels could also be used. It can be advantageous to use lower power levels where less highly trained users are operating the system. For example, powers of up to 6 W/cm$^2$ may be used with exposures much longer that 5 seconds without reaching unsafe epidermal or dermal temperatures. This means that a range of treatment powers exist at which the sapphire block could be held in contact with skin for a long period, measuring many seconds or even minutes, elevating the dermis to some constant, relatively mild temperature distribution.

Filament Power Control & Safety Features

As described in detail above one embodiment herein provides for a filament energy source, where electromagnetic energy is generated by driving a current through the filament. In many embodiments it can be desirable to be able to have some control over the operation of the filament lamp.

Resistance Control

It can be desirable to heat the filament quickly when performing a dermatology treatment with a filament lamp, because controlling the optical power output by the lamp requires the filament to be hot enough to emit significant radiant power. In order to quickly raise the temperature of the filament, it can initially be driven with an electrical current capable of destroying the filament should it be applied to the filament for long periods of time.

One method of preventing overheating and subsequent failure of filaments is to measure or derive the filament resistance, which is a function of the filament temperature, and to use this resistance value as one input to control the power source. The pulse width modulation operation of the filament lamp by the HVPS can then "resistance regulated". No photometric monitoring is required in this mode. If photometric regulation is employed, resistance regulation may serve as a redundant check on the filament to protect against filament failure. In one embodiment the system includes a filament lamp which is connected to a power source, and the power source is electronically controlled to drive the filament lamp to output electromagnetic energy. The system also includes a sensor which outputs a signal corresponding to the resistance of the filament. In one embodiment the resistance sensor would operate to measure an instantaneous current through the filament, and an instantaneous voltage drop across the filament, and the resistance is determine by the voltage divided by the current. Although not shown in FIG. 11, a resistance sensor could, in one embodiment, be included in a system such as that of FIG. 11, where the resistance sensor would be coupled to the filament of the filament lamp 1104, and the output from the resistance sensor would be transmitted to the controller 1112. In one embodiment the resistance sensor could be used in place of photodetection, and in another embodiment the resistance sensor could be used in addition to photodetection. The power supply is operable to reduce the electrical current in response to a signal indicating that the resistance of the filament is increased beyond some specified value.

Filament Failure

In one embodiment, the filament lamp is driven by a high voltage power supply as described above; such an HVPS could also be designed to drive xenon flashlamps and Xe flashlamp driven lasers. As a result of using such a versatile power supply, it is possible that the voltage operating range for the HVPS will be quite high. In the event of a filament failure, the Xe/halogen gas in the filament lamp may continue to support current flow by establishing an electrical arc inside the tube. Uncontrolled arcing inside the lamp represents a potentially system-damaging event, while intense short-wavelength radiation from the arc represents a potential exposure hazard for the patient. One safety aspect of the invention is to use electrical pulses, where the pulses are short enough relative to a time period between the pulses, so as to allow any initial arcing to extinguish after a single pulse. The energy then available in a subsequent pulse is then low enough to avoid any hazard in the event of filament failure.

In one embodiment, one aspect of a safety circuit is that it senses when the lamp voltage (or resistance) has risen out of acceptable limits while it is being driven by the HVPS. This is also an indication of an open or high resistance filament.

Another aspect of the safety circuitry provides for a ground fault detector to remove power from the lamp when a ground fault is detected.

Anti-Condensation Plate

As discussed above, it is desirable to protect the epidermis during treatments by controlling the epidermal temperature. In one embodiment as discussed above, a sapphire window is provided and is placed in direct contact with the skin. Electromagnetic radiation is transmitted through the sapphire block and applied to the skin. The sapphire window is temperature controlled using cooling devices in contact with the sides of the sapphire window, maintaining a safe epidermal temperature. In some versions, thermoelectric coolers may be used. In other versions chilled coolant may be used.

In one embodiment it is desirable to have the epidermal control temperature be relatively high so that the dermal heating by the infrared lamp does not have to overcome a low dermal temperature imposed by the cooling. In order to reduce, or avoid, bulk cooling, that would have to be overcome by the EM source, the low end of the cooling temperature range is set at approximately 15 C.

On the other hand, using an epidermal cooling temperature that is too high potentially places a restriction on the type of cooling mechanism used to cool the sapphire window. Specifically, if the control temperature is higher than room temperature, or higher than the temperature of the console heater exchanger, uni-directional cooling cannot be used. This simply means that cooling mechanisms that can cool, but not warm (i.e. chilled coolants, uni-directional TECs), cannot be used.

This conflict between these two requirements on epidermal control temperature can be resolved by employing cooling mechanisms that are bi-directional (both cooling and warming capable). Such a requirement increases the system complexity and cost.

An approach taken in another embodiment is to simply operate at a temperature between the two limits described above (e.g., not so cool so as to create bulk cooling which might be difficult to overcome, and not so warm as to be of higher temperature than some environment where treatment environment is actually cooler than room temperature). In one embodiment the two limits are set in a range of practical epidermal cooling temperatures between 15 and 25 C.

Unfortunately, water condensation on the sapphire window/block represents a potential problem for this temperature range. Water condensation problems are exacerbated by the following factors: (1) treatments require relatively long exposure times and near continuous contact with aqueous gels, (2) hermetic sealing of a hand piece to prevent condensation is difficult to achieve, (3) any condensation appearing on the sapphire is potentially very problematic given that water is the chromophore used in the treatments, (4) the spectral output profile, partially produced by filtering with the thin, controlled layer of water coolant surrounding the infrared lamp, may be adversely affected by any condensation which could in effect add additional filtering.

Previous approaches to this problem include insulating the cooled window from water vapor with a second window or optic. Typically the space between the cooled window and the insulating window is a gas or vacuum. U.S. Pat. No. 6,770,069, entitled Laser Applicator, by Hobart and Negus, describes a number of such approaches, and is incorporated herein by reference.

In order to reduce or prevent condensation an embodiment of the present invention employs a secondary window of poor thermal conduction to support a relatively large thermal gradient at the input surface of the cooled sapphire window. The formation of condensation on the input surface of the sapphire window is thus prevented by holding this surface above the dew, or condensation, point. Typically, this requirement means at least a 25 C temperature is maintained at this surface.

Figure 14:
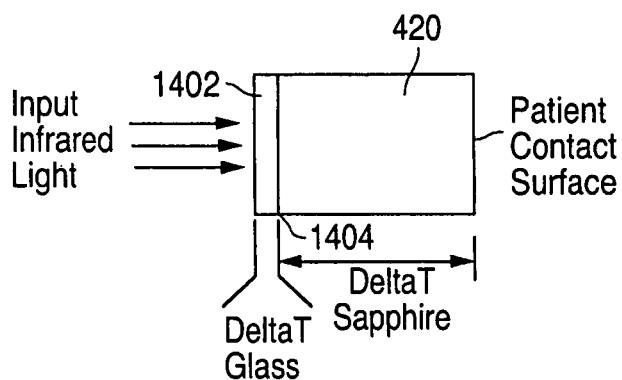
FIG. 14 shows an embodiment of a system herein with an anti-condensation plate bonded to the sapphire input surface, where the sapphire block transmits radiation to a treatment area.

An embodiment of a portion of a system herein is shown in FIG. 14. FIG. 14 shows a sapphire block 420 as described above, with an insulating layer 1402 coupled to the sapphire input surface 1404. The insulating layer 1402 can be an optically transparent glass window optically bonded to the sapphire input surface 1404 (where electromagnetic energy from the energy source is input to the sapphire block 420). The glass window operates as an anti-condensation plate, and supports a moderately strong thermal gradient across the material of the glass window 1402. The material insulating layer should have a low enough thermal conductivity such that even for a relatively low thermal loading on an input side of insulating layer a relatively large thermal gradient ($\Delta T/\Delta X$) is maintained across the thickness of the insulating layer 1402. The glass window 1402 has a sufficiently poor thermal conductivity and thickness combination to allow for at least a 5 C temperature difference between the front (where the energy is input) and back (which is bonded to the sapphire block 420) surfaces of the glass window when thermal loads of at least 1 Watt are applied to the glass window (1 Watt represents a minimum in the thermal load that the lamp reflector air space presents to the input surface of the sapphire simply due to the warm air in the vicinity of the lamp.)

The glass chosen should have a poor thermal conductivity, and should also be thin enough to avoid making the optical assembly overly large or thick. Borosilicate glasses, such as Pyrex, are good choices, while relatively conductive glasses, such as fused silica, are poor choices. Borosilicate glass from 1 mm microscope slide glass allows for at least an 8 C temperature difference ($\Delta T$) at the input surface of the optical assembly, assuming at least a 1 Watt/$cm^2$ thermal load at the assembly input surface.

A simple estimate of the temperature delta across piece of 1 mm borosilicate glass optically cemented to the sapphire window:

| | |
|---|---|
| thermal conductivity (k): | 0.8 W/m*deg C. |
| glass dimensions: | 1.5 $cm^2$ × 1 mm thick |
| heat load to glass input surface (Q/Area): | 1 W/$cm^2$ |
| Q/A = k $\Delta T/\Delta x$ | –>> $\Delta T_{glass}$~8 C. |

This same heat load produces only a 0.25 C temperature rise front-to-back across the thickness of the sapphire window ($\Delta T_{sapphire}$.)

Thus, for an embodiment as shown in FIG. 14 where anti-condensation plate 1402 is optically bonded, such as by using an optically transparent adhesive, to the sapphire window 420, and the delta T of the glass (front-to-back) under a typical heat load is 8 C. A 20 C sapphire block then results in the glass window input face being held at about 28 C, which is safely above the dew point for almost any operating conditions.

An advantage of this using the insulating layer 1402 is that condensation is prevented while avoiding additional thermal load on the sapphire/cooling mechanism that other approaches might generate (such as, heating the input end of the sapphire.)

The anti-condensation plate can also be made of a material which is selected so as to provide for efficient transmission of light into the sapphire block. In one embodiment the anti-condensation plate is made of a flint glass such as SF 11, which combines excellent light guide properties (e.g. high index of refraction) with low thermal conductivity.

The refractive index of flint glass is high: for SF 11 it is n=1.745 at 1529.6 nm, and for sapphire it is n=1.7466 at the same wavelength. This means the anti-condensation plate will guide light in approximately the same manner as sapphire.

The angle of total internal reflection determines a light guide's efficiency,

| | | |
|---|---|---|
| $\Omega = \operatorname{asin}(n(\text{air})/n(\text{sf}11))$ | Sapphire = | 34.49 degrees |
| | SF 11 = | 35.00 degrees |

Borosilicate glass, such as BK7, has a much lower index, around 1.54, which yields a total internal reflection of 40.49 degrees. The acceptance angle for SF11 relative to the acceptance angle for BK7 is approximately 15.7% greater.

Also, the thermal conductivity of SF11 is =0.737 W/m*deg C., which is lower than the borosilicate example, and should provide for increased anti-condensation properties.

Cooling of Lamp Quartz Envelope

Some embodiments of the invention employ quartz tungsten halogen (QTH) lamps as the infrared light source. QTH lamps require a "halogen cycle" to prevent deposition of evaporated tungsten particles from adhering to the lamp interior wall. Aspects of this operation are discussed in "Illumination Engineering—From Edison's Lamp to the Laser" at pp. 208-211, by Joseph B. Murdoch, Macmillan Publishing Company (1985), which is incorporated herein by reference.

As discussed above an embodiment herein uses a liquid coolant element in contact with a QTH lamp envelope. The reasons for this type of cooling are: (1) the need to remove the bulk of the heat load dissipated in the hand piece itself, since most of the light/heat generated by the QTH lamp is not useful and desirably removed, and (2) use of a controlled thickness water annulus to perform part of the wavelength filtering function. The latter allows for strong water absorbing wavelengths emitted from the lamp to be removed. These strongly absorbing wavelengths if left unfiltered could largely result in undesirable epidermal heating.

A consequence of lamp cooling performed with water flowing across the lamp in an annulus is that the lamp exterior wall temperature is reduced because of the temperature of liquid water. Unfortunately, the halogen cycle does not work well for interior quartz wall temperatures below 500K. Generally the halogen cycle begins area at around 250° C. and can range up to about 800° C. It has been found that lamps will degrade quickly at temperatures where the interior quartz wall is below about 500° K, under such conditions, darkening (due to tungsten deposits) the envelope wall and decreasing the optical output.

One solution is to decrease the lamp coolant flow to a point at which the cooling and wavelength filtering is adequately performed, but the lamp wall temperature is allowed to rise, while remaining comfortably below the boiling point of the coolant. This higher temperature improves the lamp degradation to a point at which operating the lamp becomes practical for medical applications (>10,000 exposures.) An embodiment herein provides for balancing multiple factors to determine the rate of coolant flow; these factors include: (1) the proper thickness for water wavelength filtering (between 0.25 and 1 mm, preferentially in the range of 0.5 mm), (2) heat removal from the lamp (removing a heat load of 50 W<heat removed<400 W), and (3), slow enough water flow to allow the temperature of the lamp wall to approach 100 C, the boiling point of the cooling.

An alternative embodiment could use a mixture of water and ethylene glycol or alcohol to allow the coolant temperature to rise even further, since water-admixture boiling points are higher than pure water. Another potential advantage arises from the use of water-admixture, instead of pure water. This advantage arises from the fact that for one embodiment using pure water provides that, for a desired amount of filtering, a thickness of water should be about 0.5 mm. In application it can be difficult to maintain manufacturing process to achieve a 0.5 mm thickness for the region where the water is disposed. Where water add mixture is used a the amount of filtering achieved per thickness of liquid is reduced, so the thickness of the liquid region can be increased to about 2.0 mm to achieve the desired amount of filtering, and with this increase in spacing it can be easier to maintain consistency in the manufacturing process, as tolerances for the thickness of the liquid region can be loosened.

Figure 17A:
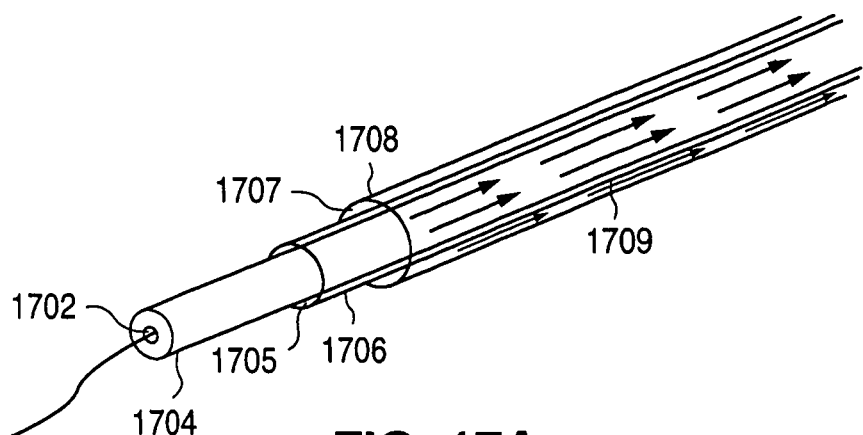
FIG. 17A-C show an embodiment of a two tube cooling system herein.
Figure 17B:
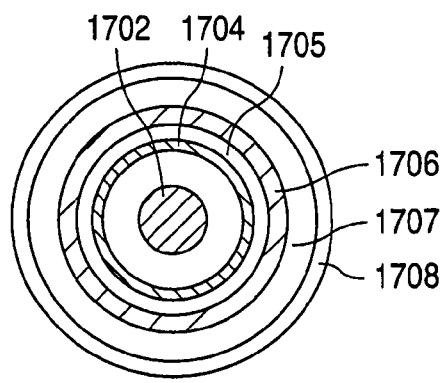

One challenge with the above approaches is that to some extent they may limit the ability to cool the hand piece to a desired temperature. An embodiment is shown in FIG. 17A-B which provides for another way of providing for cooling and still allowing the quartz envelop to reach a sufficient temperature for the halogen cycle. Specifically FIG. 17A shows an isometric cutaway view of the filament lamp, which includes the filament 1702 and the quartz envelop 1704. An annular sleeve 1706 is then provided surrounds the quartz envelope. The annular sleeve, or tube, can be formed of different materials such as quartz, sapphire, or glass. The diameter of the annular sleeve 1706 is greater than the diameter of the quartz envelope 1704, such that a gap 1705 is created between the quartz envelop 1704 and the annular sleeve 1706. A second annular member 1708 is then disposed around the annular sleeve 1706. The diameter of the second annular member 1708 is of a greater diameter than the annular sleeve 1706. A cooling liquid, such as a flow of water 1709 can then be disposed in the gap 1707 between the annular sleeve 1706 and the annular member 1708.

The concentric tube structure of FIG. 17A is further illustrated in the cross sectional view shown in FIG. 17B. As shown in FIG. 17B a filament 1702 is enclosed by a lamp envelope 1704. The annular sleeve 1706 then surrounds the lamp envelope which forms a gap 1705 between the lamp envelope 1704 and the annular sleeve 1706. The gap 1705 can be filled with a gas, air or liquid which could be circulated, but in some embodiments it would not be circulated. The gap region 1705 operates to allow the lamp envelope 1704 to reach a sufficient temperature for the halogen cycle. The gap 1707 between the annular sleeve 1706 and the annular member 1708 can contain a flowing coolant. The lamp heat is radiated or conducted across gap 1705 and through the sleeve 1706 into the gap 1707 which is cooled by the flowing liquid. This allows high temperatures for the lamp envelope 1704 while the cooling of the handpiece can be achieve using the cooling fluid which removed a short distance from the surface of the lamp envelope.

Figure 17C:
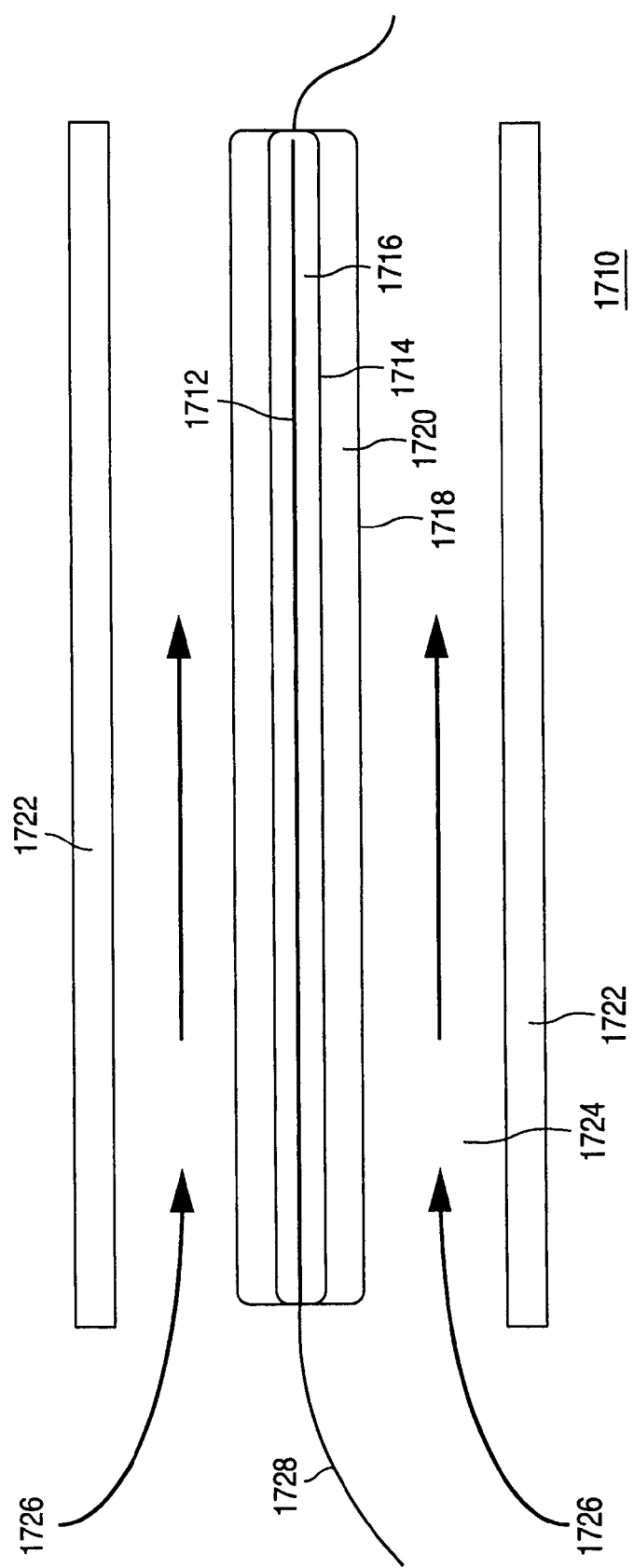

FIG. 17C shows an alternative embodiment 1710, similar to the two tube structure in FIG. 17A. However, embodiment 1710 utilizes a double walled lamp envelope which operates to provide an insulating gas region adjacent to the portion of the lamp with the quartz envelope tungsten filament halogen region. The filament 1712 is disposed in a first quartz envelope 1714, and an electrical lead 1728 is provided to the filament 1712. The halogen gas of the lamp is disposed in region 1716 inside the first quartz envelope 1714. A second quartz envelope 1718 is then provided around the first quartz envelop, forming a closed insulating gas region 1720 which is electrically isolated from the halogen region 1716. An outer annular sleeve 1722 is then disposed around the second quartz envelope 1718, and in the region 1724 between the second quartz envelope and the outer annular sleeve, cooling fluid flow for cooling 1726 can be provided. This design can allow for sufficient heating of the first envelope 1714 while the second envelope 1718 provides for containment of the cooling and filtering fluid away from the first envelope.

Shutter Element

An alternate embodiment of the filament lamp treatment device would use a shutter device to control the flow of electromagnetic energy from the lamp to the skin. The shutter would be located in the optical path between the lamp and the treatment area. When the shutter is in the closed position, it would prevent the treatment energy coming from the lamp from reaching the treatment area. In the open position the shutter would allow the treatment beam to reach the patient. The shutter device can be electromechanically actuated, and the duration that the shutter is open or closed could be determined by a timing circuit.

One of the inputs controlling shutter position could be feedback from a photodetector that receives at least part of its light from the treatment lamp. Alternatively, or in addition another input controlling shutter position could be a temperature measurement of the window in contact with the patient.

Figure 9A:
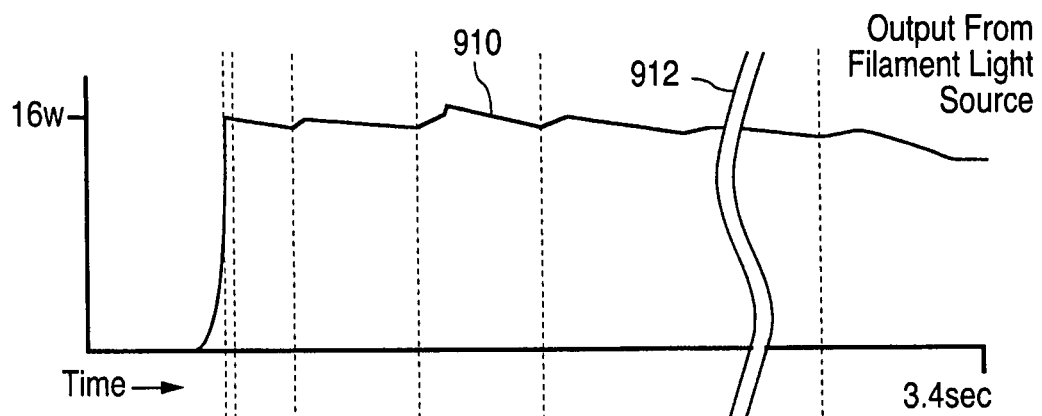
FIG. 9 illustrates the driving of a filament light according to an embodiment herein.
Figure 9B:
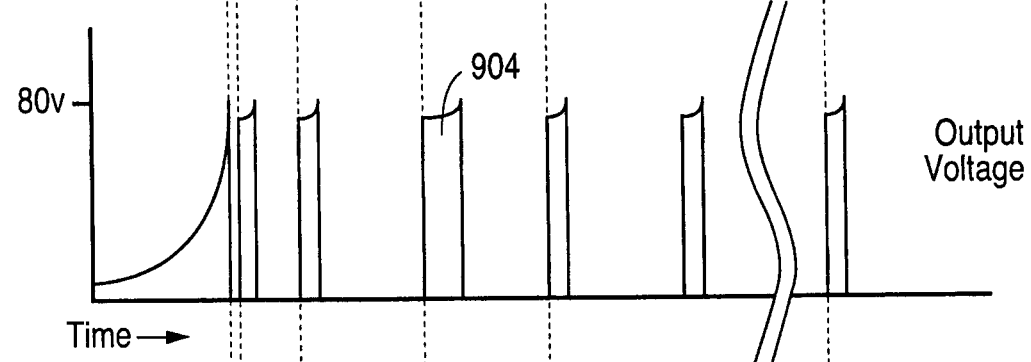
Figure 9C:
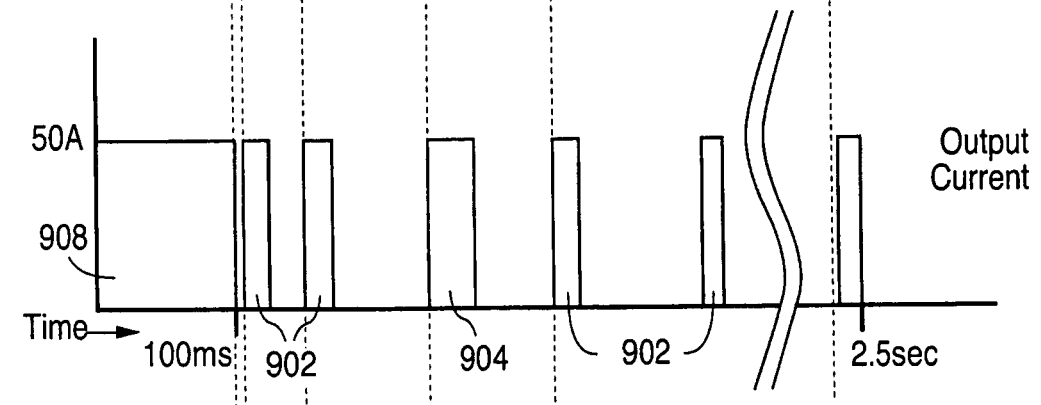

One benefit of using a shutter to control the transmission of electromagnetic energy to the treatment area is that the shutter provides a relatively simple mechanical structure, that allows the system to easily regulate the amount of energy transmitted to the skin. As shown in FIGS. 9A-9C and as discussed above, a significant amount of EM can continue to be emitted from the filament lamp for a time period after electrical current has stopped being applied to the filament. This can be a significant amount of energy which is many treatments should be taken into account. An alternative embodiment using a shutter could utilize a power supply which operates to continuously apply current or pulses of current to the filament. In such a system the shutter could simply be opened to allow for the transmission of EM to the area being treated, and then the shutter could be closed to stop the transmission of EM to the skin. In such a system the lamp could essentially remain on for an extended period of time and the shutter would be opened and closed and as the device is moved over areas of skin to be treated.

Acne Treatments

Moderate warming of the epidermis and dermis can have a beneficial effect on acne by producing injury to sebaceous gland(s) (See, e.g., Javier Ruiz-Esparza and Julio Barba Gomez, "Nonablative RF for Active Acne Vulgaris: The use of Deep Dermal Heat in the Treatment of Moderate to Severe Active Acne Vulgaris (Thermotherapy): A Report of 22 Patients," American Society for Dermatologic Surgery, Inc. 29:4 Apr. 2003, which is incorporated herein by reference).

More superficial and stronger skin heating produced using lasers such as the 1450 nm laser diode has been used to treat acne. Photoselectivity of the sebaceous gland may not be a requirement for such treatments. Confining thermal damage or thermal injury to the depths at which glands are located has been suggested as a mechanism for treating acne (See, e.g., D Y Paithankar, E V Ross, et alia, "Acne Treatment with a 1.450 nm wavelength Laser and Cryogen Spray Cooling," Lasers in Surgery and Medicine, 31:106-114, 2002, which is incorporated herein reference). In much of the previous literature regarding use of lasers for treating acne the general operational approach has been to apply millisecond long pulses of energy to the area being treated, where the energy operates to provide for relatively high, in the range of 80° C. temperatures, at relatively shallow, upper 0.5 mm, of the skin. Arrhenius thermal damage (as described above) can be achieved at lower temperatures than the 80° C. range, if the exposure duration is sufficiently long. Exposures of many seconds duration in the 45-60° C. range can be used to produce the thermal damage equivalent to much shorter exposure durations of pulses<100 ms with temperatures in the 80° C. range. The advantage is that lower temperature exposures may be performed more safely.

Thus, an embodiment herein can be used to apply lower temperature (45-60° C. range) acne treatment to a treatment area, where the combination of the energy source, for example a filament lamp, and the cooling of the sapphire block, and possibly using filtering to remove strongly absorbed wavelengths, allows for controlling and maintaining a treatment temperature in tissue being treated in a range of between approximately 45-60° C., for significant period of time. Where the treatment time for an application of EM energy would be greater than 1 second, and preferentially in a range of 2-5 seconds or longer to sufficiently damage the sebaceous gland and thereby reduce acne.

Hand Held Embodiment Including Power Supply

Figure 15:
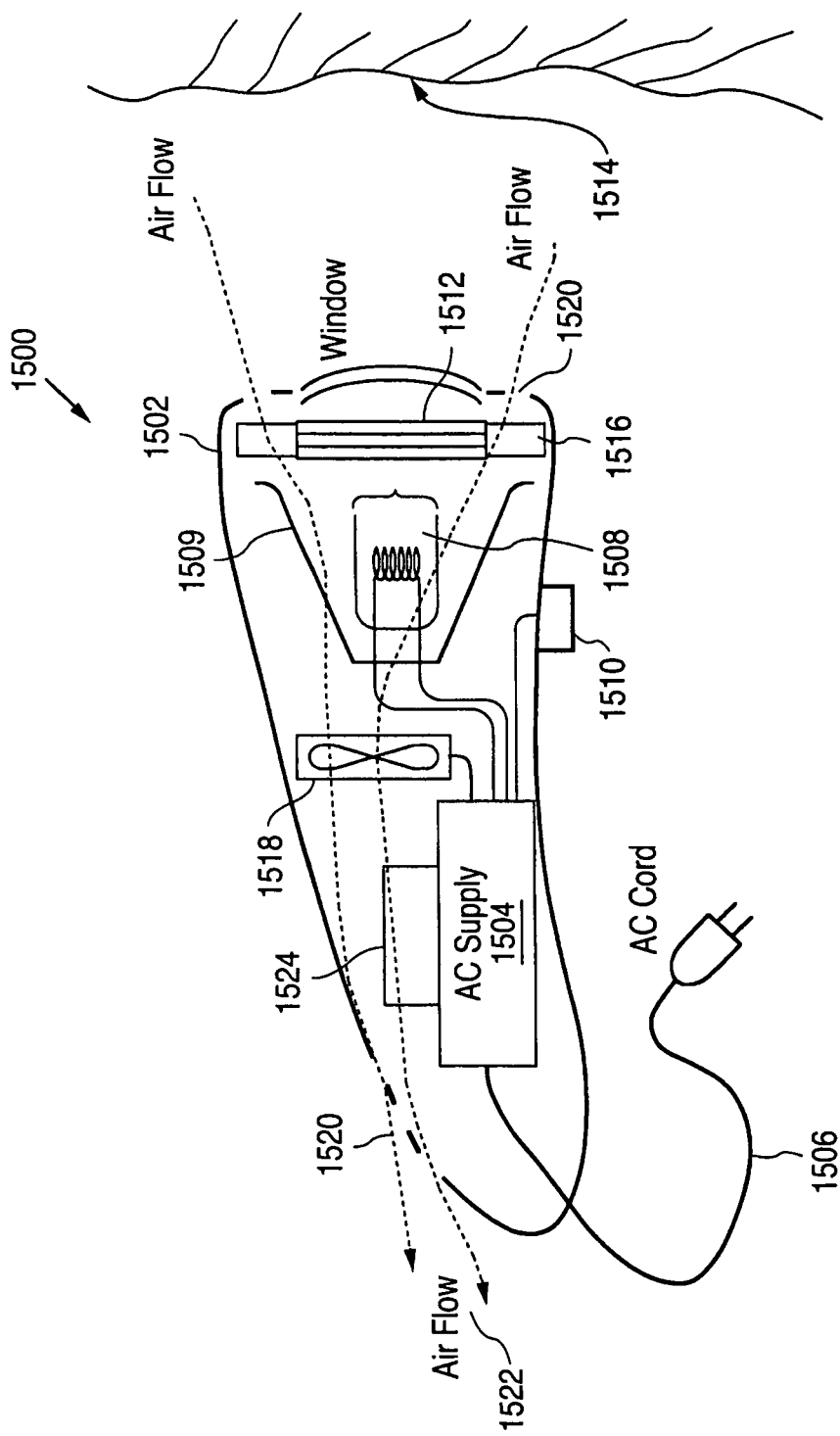
FIG. 15 shows an embodiment of a system herein having the power supply mounted in the handpiece which applies the treatment radiation to the treatment area.

FIG. 15 shows an alternative embodiment 1500 of a system herein. The system 1500 provides for a simplified and lower cost design, which provides for lower lamp power. The system 1500 provides for an ergonomically shaped housing 1502, which can be shaped as handpiece suitable for extended periods of being held while the treatments are being applied to the skin. The other elements of the system can be secured in the housing. The system can be powered by AC power supply 1504, which receives AC power via a power cord 1506, which can be plugged into a conventional 120 volt wall outlet. Alternatively, a battery driven power supply could also be utilized, where the batteries could for example, be removably secured in the housing 1502. Aspects of a suitable shape for hand held device which includes all of the elements of an electromagnetic skin treatment system are described in more detail in co-pending U.S. patent application Ser. No. 10/794,882, filed Mar. 5, 2004, entitled SYSTEM AND METHOD FOR LOW AVERAGE POWER DERMATOLOGIC LIGHT TREATMENT DEVICE, which is incorporated herein by reference in its entirety.

The embodiment of system 1500 is particularly suitable for lower power applications utilizing infrared and/or near infrared electromagnetic energy. One example of such an application is the treatment of acne. Aspects of the treatment of acne are discussed in co-pending application Ser. No. 10/782,534, filed Feb. 19, 2004, entitled METHODS AND DEVICES FOR NON-ABLATIVE LASER TREATMENT OF DERMATOLOGIC CONDITIONS, which is commonly assigned, and is incorporated herein by reference in its entirety.

The system 1500 drives the filament lamp 1508 with a lower amount of electrical energy than more high power systems, whereby the optical power delivered is in the range of 2-10 W/cm². At this level of optical power the system 1500 is suitable for use by novice or untrained users. Specifically at the power density of 5 W/cm², repeated exposure would not heat skin unsafely with cooling. Further, at lower power densities, in the range of 3 W/cm², treatment could safely be provided without the need for epidermal cooling to protect the epidermis from overheating.

The exposure switch 1510 controls each exposure. Repeated exposures would be timed to maintain accumulated thermal doses below safe limits. Specifically, in one embodiment the power supply is provided with a simple processor which sets a maximum of electrical current which will be provided to drive the lamp per a given amount of time.

Given the significantly lower power levels of the system 1500 as compared with the other embodiments described above, the issues related to the cooling of the system and the skin are considerably simplified. As described, some of the higher power embodiments utilize a water cooling loop, with water flowing in an annular channel around the filament lamp. The lower power system does not require a water cooling loop. However, a water filter can still be utilized in the lower power system 1500. Specifically, in one embodiment a filter assembly 1512 is disposed between the filament lamp 1508 and the area of skin 1514 to which the electromagnetic energy is applied. The filter assembly includes elements selected to filter out specific ranges of electromagnetic energy emitted by the filament lamp 1508. One of the elements of the filter assembly is a thin layer of NIR-absorbing water. In one embodiment the filter assembly uses a water "sandwich" to perform this part of the filtering. Coatings applied to the exterior surfaces of the filter assembly perform the balance of the filtering. The absorbing nature of the water NIR filter portion places a requirement of heat removal on the filter assembly 1512. Because the overall heat load is relatively low, the mass of water and filter that must dissipate the absorbed heat is small. Thus, heat sinks 1516 can be included in the filter assembly. In one embodiment the heat sinks are provided with channels through which air flows, and the air current is created by a fan 1518 which is disposed in the housing 1502. The housing 1502 is also provided with openings 1520 to allow for air flow 1522 through the system 1500. Further, the power supply 1504 can be coupled with a heat sink 1524 to provide for dissipation of heat generated by the power supply. A reflector 1509 which is perforated for air flow can also be provided.

Additional Treatments

The above discussion provides for a range of different systems and methods of treatment. Some additional details are further provided below for targeting and treating lax or redundant post-partum skin. It should be recognized that the discussion provided above is applicable to treating post-partum skin as well as a range of other different areas of skin. Further, some of the principles discussed above could be used with different types of EMR sources, such as RF sources, lasers, flashlamps, LEDs, laser diodes, as well as filament lamps.

In general, where treating post-partum skin, according to a method herein, the thermal profile created by the application of EMR, and the cooling surface applied to the skin, is an inverted thermal gradient, with the upper layers of the epidermal tissue at a lower temperature than deeper dermal layers. An inverted thermal gradient can provide continuous variation in temperature as a function of skin depth, in which the superficial layers of the epidermis and dermis are at lower temperatures than the deeper layers. Thus, the epidermal temperature is held to a safe level while the dermis is heated to a treatment temperature by the EM radiation. Specific illustrative embodiments of systems for providing such an operation are provided above. In one embodiment optimal heating of the tissue to be treated is produced through control of the absorption depth profile associated with the penetration of the applied EM radiation to the skin. The temperature profile and its duration affect the lax skin in such a way as to reduce, or reduce the appearance of, the excess skin. Desired depth profiles produce significant temperature rises at depths of up to 5 millimeters, and in some embodiments it may be desirable to provide treatment temperatures at even deeper levels of tissue. In many instances the treatment will typically target providing for significant temperature increases at depths ranging from 1 mm to 5 mm.

Peak dermal temperatures are at least 40 C, with practical ranges falling between 40 and 70 C, and it is generally preferable for the treatment temperature to be at least 50 C. Duration of the EM exposure ranges from 1 to 20 seconds. The time and temperature history during the exposure determines the degree to which redundant skin is effected, and therefore the degree of reduction, or the appearance of reduction of the redundant skin. In addition to treating loose abdominal skin, the systems and methods herein for treating post-partum redundant skin can be used to treat areas with relatively large areas of loose skin, such as areas under the upper arms; folded, redundant skin over the patella; upper thigh and buttocks.

One embodiment of the system and method herein would provide for using a device such as that shown in FIG. 4. An electrical current would be applied to the filament 404 of the device. In response to the electrical current through the filament optical energy would be generated. The output area of the outer surface 430 of the sapphire block 420 would be placed in contact with the area of lax abdominal skin to be tightened. The sapphire block would also provide for cooling of the epidermal layers of the abdominal skin being treated. Aspects of the operation of the embodiment of the treatment device shown in FIG. 4 of are described in more detail above.

In one embodiment the application of the EM radiation to the lax post-partum tissue should bring the tissue in the depth range of 1-5 mm to a temperature of at least 50° C. In one embodiment the EM radiation applied to the tissue would be controlled, as discussed above, so that the temperature of the tissue being treated would be held in the range of 55-65° C. for a number of seconds typically in the range of 1.2 to 20 seconds, while the sapphire block, or other cooling mechanism would operate to hold the upper surface of the area skin being treated at a safe temperature.

Figure 18A:
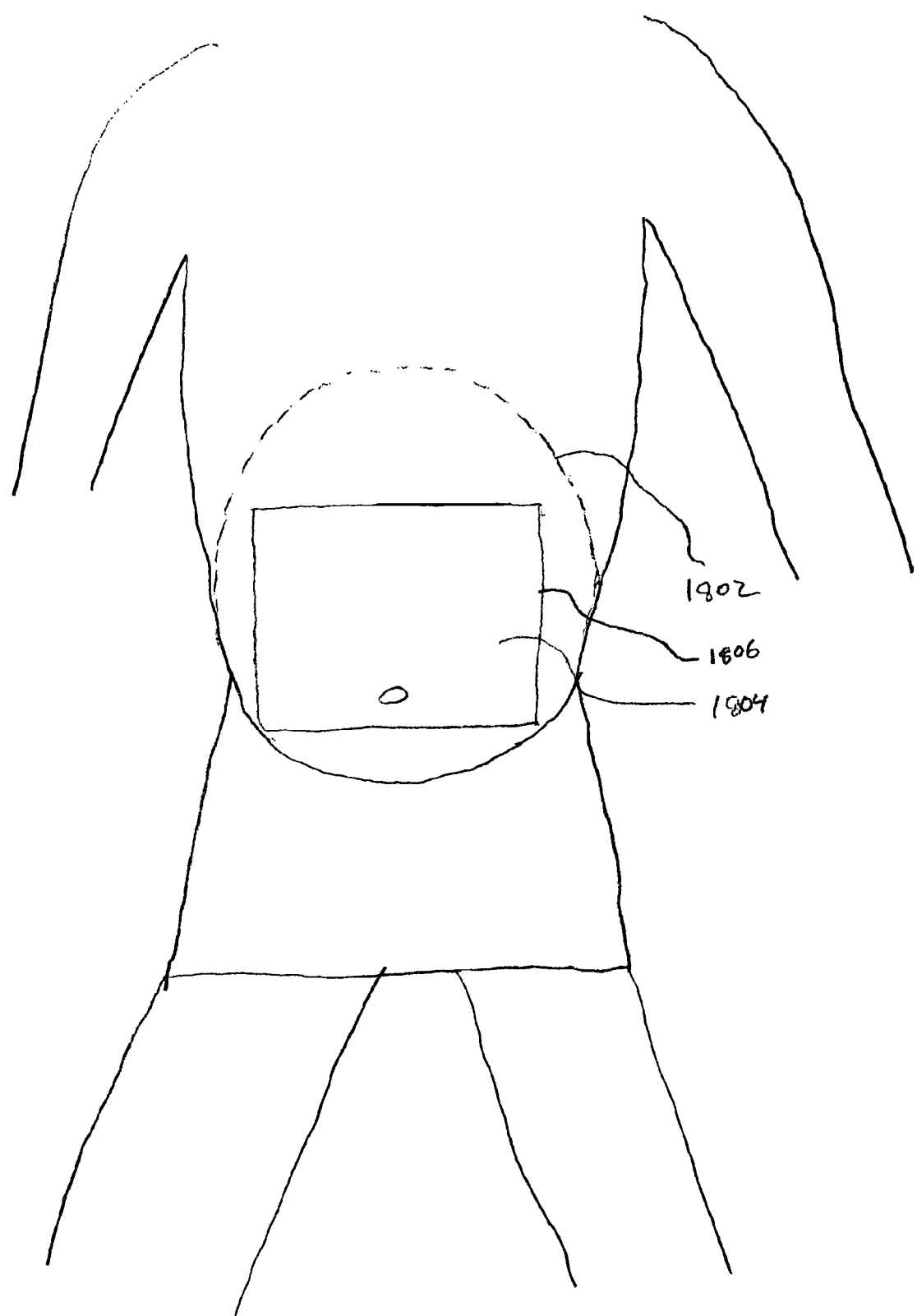
FIG. 18A-B illustrates an embodiment of a method herein for treating post-partum redundant abdominal skin.
Figure 18B:
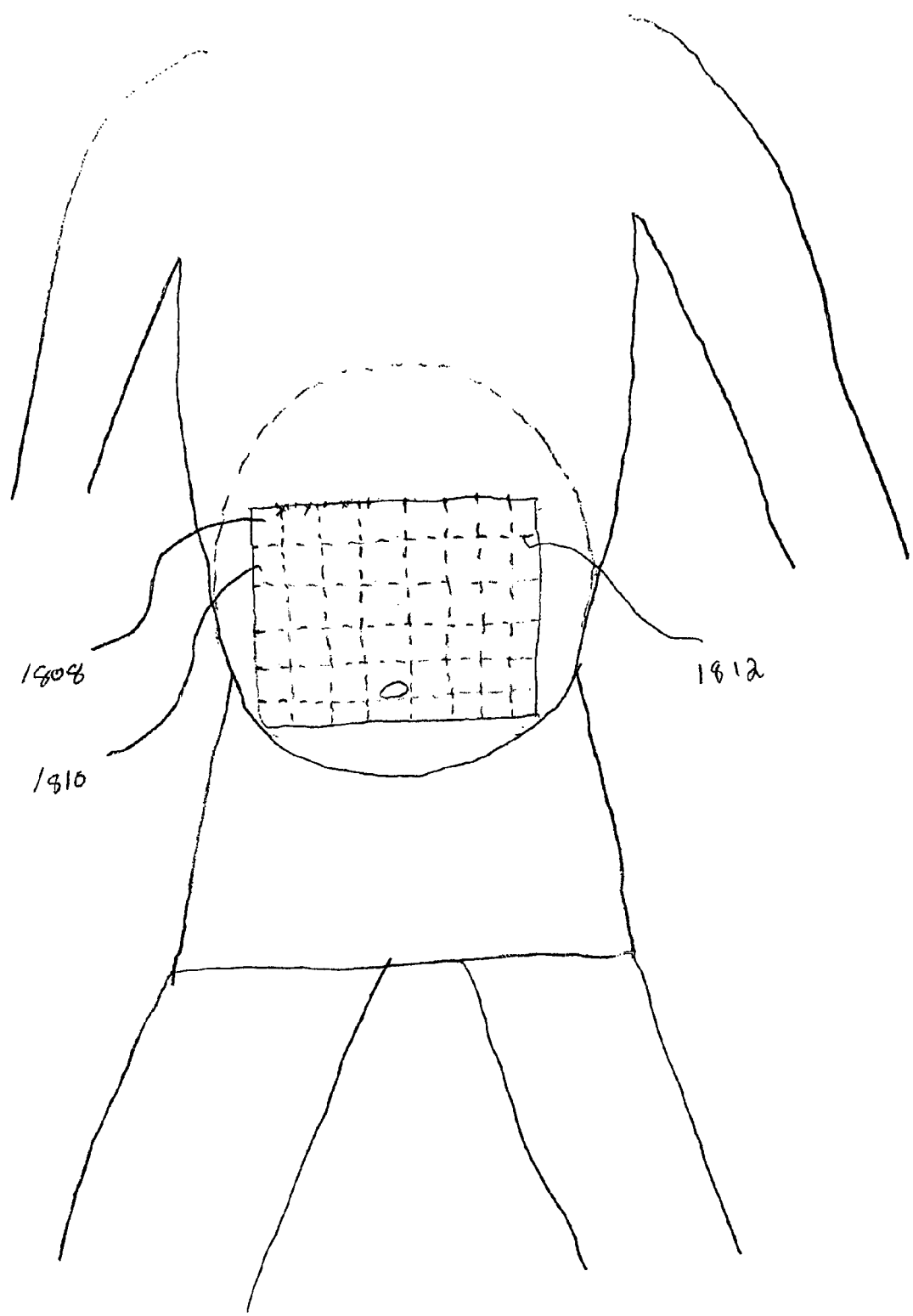

Contemplating use of a device such as that shown in FIG. 4 some specific exemplary treatment parameters will be discussed. In one mode of operation an area of lax abdominal skin is identified and pulses of EMR are applied to adjacent sub-areas of abdominal skin within the identified area of lax abdominal skin. FIG. 18A shows a general illustration of a treatment area. Initially an area of abdominal tissue 1802 is analyzed. Typically, the area of treatment will be identified as a central area 1804 of the abdominal skin. In order to provide a clear identification of the area of abdominal tissue to be treated it can be helpful to mark 1806 the area for treatment. This marking can be done using a variety of different washable marking pens for example. After the area for treatment has been identified a gel can be applied to the area 1804 to be treated. This gel can serve to enhance the coupling of the treatment device with the area to be treated. In some instances the gel can optionally not be applied. The treatment device, such as that shown in FIG. 4, can then be used to apply treatment exposures to adjacent areas of skin located within the area identified for treatment. In one embodiment each treatment exposure will bring a sub-area to which the treatment exposure is applied to a temperature to at least 50 C, in a depth range of 1-5 mm, while the tissue at more shallow depths will be held to cooler temperatures. For example, a first treatment exposure could be applied to a sub-area of tissue shown as 1808, in the dashed grid lines shown in FIG. 18B in the area 1804 to be treated. The dashed grid lines 1812 are shown to illustrate a number of adjacent treatment sub-areas within the area 1804 being treated. Typically, the treatment exposures would then be applied sequentially across the top row of the grid of sub-areas. Subsequent to application of the treatment exposures to the adjacent sub-areas in the top row of the grid, the treatment exposures would then be started in the next row down, which includes treatment sub-area 1810. This process would be continued until a pass had been completed across the entire area 1804. In many instances a treatment session will consist of two or more passes of treatment exposures across the area 1804 to be treated. It should be noted that while the adjacent sub-area area shown as being contiguous, in some instances the exposures could be applied such that there is some spacing between sub-areas, or some overlap between adjacent sub-areas. It should be noted that some treatment methods can provide for identifying a relatively large area for treatment, where some of skin in the identified area is lax, and some of the skin is relatively tight. In some instances the treatment could then provide for applying treatment exposures to the relatively tight skin, and the effect could be to tighten the skin an adjacent area of relatively lax skin.

While much of the discussion herein contemplates identification of areas for treatment based on the visual appearance of redundant or lax skin, which in some instances will appear to be baggy or wrinkled skin, it is not in fact a prerequisite that an area have this type of appearance prior to a treatment being applied. Indeed, in the case of treating post-partum redundant skin, it is sometimes the case, that the abdominal skin will not appear to be overly lax, wrinkled or baggy for a number of months following a pregnancy. However, after a number of months, or in some cases years have passed, the trauma to the skin during the pregnancy coupled with the effect of gravity can lead to cause an increase in the visual indications of post-partum skin redundancy. In some instances, it is believed that it can be advantageous to treat an area of the abdominal tissue prior to the appearance of strong visual indications of part-partum abdominal skin redundancy. In the initial months following a pregnancy the epidermal and dermal layers of the skin, and the collagen in this tissue area, are stretched and in the process of contracting. During this time period the treatment exposures can be applied to the skin, and thereby reduce some the appearance of post-partum skin laxity, which might otherwise occur at a later date.

While in one embodiment the typical surface area of the lax abdominal skin can require in the range of 50 adjacent pulses to cover an average area of abdominal skin tissue to be treated, it should be noted that the number of adjacent pulses necessary to treat an area of lax abdominal tissue will vary from patient to patient, and depend on the size of the area to be treated. Further the size of EM radiation source could also vary in different systems, and with larger EM radiation output areas the number of adjacent pulses required to cover a treatment area would be reduced. Once a first pass treatment has been completed a number of additional treatment passes can be applied, where a pass generally corresponds to applying multiple treatment exposures which combine to cover the area being treated. In one exemplary embodiment 3 or 4 treatment passes will be applied to the area of abdominal tissue. The fluence for each applied light treatment exposure in one embodiment is in the range of 42 to 46 J/cm2. In another embodiment a range of fluence for each application of EM radiation is in the range of 38 to 50 J/cm2. Where a patient can tolerate higher fluence level, it is generally preferable to select higher fluences. In general the patient should be able to tolerate the treatment with no more than a moderate level of discomfort.

In many cases, it will be advantageous, to perform 2 or 3 treatment sessions (where each session can include multiple passes) at roughly monthly intervals. The interval between sessions can be varied as is determined suitable for a particular treatment, but generally it is advisable to let a sufficient amount of time to elapse between sessions, so that the effect of a treatment session can be evaluated. It has been found that subsequent treatments can yield additional reduction in the appearance of skin laxity.

In one instance a patient having lax abdominal tissue from having been pregnant some 23 years earlier was treated over a large area of abdominal skin exhibiting post-partum redundancy. An initial treatment session provided for application of 4 treatment passes over the identified area of abdominal tissue. The treatment passes in total provided for application of about 400 adjacent exposures of EM radiation, and a moderate fluence level of 44 J/cm2 was provided with each exposure. The patient was provided with Tylenol #3, Toredol and Ativan for pain management. Following this initial treatment session reduction in the appearance of tissue laxity was noticeable. One month after the initial treatment, a second treatment was applied to the abdominal skin. The second treatment session provided for 4 passes of EM radiation being applied to the surface of the abdominal skin to be treated. These 4 passes consisted of 400 pulses of EM radiation being applied to the area of abdominal skin being treated. The fluence for each of the pulses during this second treatment was increased to 50 J/cm2. The 50 J/cm2 fluence level has been found to be at the high end of the range of fluences found to be tolerable by most patients. Following the second treatment session additional reduction in the appearance of laxity in the abdominal skin was apparent.

It should be noted that various different filters can be used for filtering the EM radiation generated by the light energy source, and various filter systems and energy sources providing different wavelengths of EM radiation can lead to a wide range of different fluence levels which can provide the desired treatment temperatures in skin.

In another instance a different patient with post-partum skin redundancy was treated with two passes of adjacent EM radiation exposures to adjacent sub-areas being made over the area of abdominal skin being treated. The fluence of these exposure to the sub-areas was 47 J/cm2. Within a short time after the two passes reduction in the appearance of the post-partum skin redundancy was noticeable.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents.

What is claimed is:

1. A method for diminishing laxity of an area of abdominal post-partum skin, comprising:
   identifying an area of abdominal post-partum skin having excess laxity to be treated;
   generating a broadband spectrum of near infrared electromagnetic radiation with a filament light source, said broadband spectrum continuously covering a range of at least 1050 nm to 1850 nm;
   filtering out radiation from the broadband spectrum below 1050 nm and above 1850 nm to produce a spectrum having a wavelength band consisting essentially of radiation covering 1050 nm and 1850 nm;
   and
   exposing a sub-area of the area of abdominal post-partum skin to the filtered electromagnetic radiation, wherein the exposure of filtered electromagnetic radiation is for a time period between 1.2 seconds and 5 seconds and has a fluence between 10 and 50 joules/cm$^2$ to thereby raise the temperature of a portion of a dermal layer of the skin to a treatment temperature of at least 50° C. said exposure causing a reduction in laxity of the sub-area of abdominal post-partum skin.

2. The method of claim 1, further including:
   marking the identified area of post-partum skin to be treated.

3. The method of claim 1, further including:
   applying a plurality of exposures of electromagnetic radiation to the area of post-partum skin, wherein each exposure is applied to a corresponding sub-area of the identified area of post-partum skin, and each exposure is sufficient to raise a portion of the dermal layer of the skin to the treatment temperature of at least 50° C.

4. The method of claim 1, wherein the exposure of electromagnetic radiation operates to maintain a portion of the dermal layer at a treatment temperature above 50° C. for at least 1.2 seconds.

5. The method of claim 1, wherein the treatment temperature is in the range of between 55° C. and 65° C.

6. The method of claim 1, wherein the treatment temperature is in the range between 55° C. and 65° C. and wherein each exposure of electromagnetic radiation is such that the treatment temperature is maintained in the volume of tissue for at least 3 seconds.

7. The method of claim 1, wherein the identified area is an area of redundant post-partum abdominal skin, and wherein said exposure causes a reduction of the redundant post-partum abdominal skin.

8. The method of claim 1, wherein exposing a sub-area of the area of abdominal post-partum skin to electromagnetic radiation includes exposing the skin to light energy from a halogen lamp.

9. The method of claim 1, wherein the method includes filtering the electromagnetic radiation using a water filter.

10. The method of claim 1, wherein the method includes placing a transmissive material in contact with an upper surface of the skin to be treated and transmitting the electromagnetic radiation through the transmissive material to the skin.

11. The method of claim 10, further including cooling the transmissive material.

12. The method of claim 1, further including:
    applying a plurality of exposures of electromagnetic radiation to the area of post-partum skin, wherein each exposure is applied to a corresponding sub-area of the identified area of post-partum skin, wherein the identified area is made up of a plurality of sub-areas, and an exposure is applied to each sub-area, and each exposure of sufficient to raise a portion of the dermal layer of the skin to the treatment temperature of at least 50° C.

13. The method of claim 12, further comprising:
    subsequent to applying an exposure to each sub-area, applying a second exposure to each sub-area.

14. The method of claim 12, wherein each exposure of electromagnetic radiation operates to maintain a portion of the dermal layer at a treatment temperature above 50° C. for at least 1.2 seconds.

15. The method of claim 12, wherein the treatment temperature is in the range between 55° C. and 65° C. and wherein each exposure of electromagnetic radiation is such that the treatment temperature is maintained for at least 3 seconds.

16. The method of claim 1, wherein the applying an exposure of electromagnetic radiation includes:
    generating an initial portion of the exposure of electromagnetic radiation wherein the initial portion of the electromagnetic radiation generates the treatment temperature in the portion of the dermal layer; and
    generating a subsequent portion of the electromagnetic radiation wherein the subsequent portion of the electromagnetic radiation operates to maintain the treatment temperature in the portion of the dermal layer, and wherein the treatment temperature is maintained in the portion of the dermal layer for at least 1.2 seconds.

17. The method of claim 16, wherein the treatment temperature is in the range between 55° C. and 65° C. and wherein the treatment temperature is maintained in the volume of tissue for at least 3 seconds.

18. The method of claim 16, wherein the initial portion of the electromagnetic radiation and the second portion of the electromagnetic radiation provide a continuously varying power output.

19. The method of claim 16, wherein the initial portion of the electromagnetic radiation has a first time duration and the subsequent portion of the electromagnetic radiation has a second time duration, and the second time duration is longer than the first time duration.

20. The method of claim 19, wherein the first time duration is less than half the second time duration.

21. The method of claim 19, wherein the first time duration is in the range of at least 1 second and the second time duration is in the range of at least 2.5 seconds.

* * * * *